(12) United States Patent
Hong et al.

(10) Patent No.: US 11,971,414 B2
(45) Date of Patent: Apr. 30, 2024

(54) NANOENGINEERED SURFACES FOR CANCER BIOMARKER CAPTURE

(71) Applicant: WISCONSIN ALUMNI RESEARCH FOUNDATION, Madison, WI (US)

(72) Inventors: Seungpyo Hong, Madison, WI (US); Michael J. Poellmann, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 374 days.

(21) Appl. No.: 16/771,478

(22) PCT Filed: Dec. 19, 2018

(86) PCT No.: PCT/US2018/066400
§ 371 (c)(1),
(2) Date: Jun. 10, 2020

(87) PCT Pub. No.: WO2019/126267
PCT Pub. Date: Jun. 27, 2019

(65) Prior Publication Data
US 2021/0072247 A1    Mar. 11, 2021

Related U.S. Application Data

(60) Provisional application No. 62/609,481, filed on Dec. 22, 2017.

(51) Int. Cl.
*G01N 33/574* (2006.01)
*G01N 33/543* (2006.01)
*G01N 33/573* (2006.01)

(52) U.S. Cl.
CPC . *G01N 33/57492* (2013.01); *G01N 33/54346* (2013.01); *G01N 33/5743* (2013.01); *G01N 33/57438* (2013.01); *G01N 33/57488* (2013.01)

(58) Field of Classification Search
CPC ....... G01N 33/57492; G01N 33/54346; G01N 33/5743; G01N 33/57438; G01N 33/57488
See application file for complete search history.

(56) References Cited

U.S. PATENT DOCUMENTS

2006/0269961 A1   11/2006   Fukushima et al.
2009/0247424 A1   10/2009   Chilkoti et al.
(Continued)

FOREIGN PATENT DOCUMENTS

EP        0465715 A1   1/1992
WO    2005016115 A2   2/2005
(Continued)

OTHER PUBLICATIONS

Myung et al. ("Dendrimer-Mediated Multivalent Binding for the Enhanced Capture of Tumor Cells", Angew. Chem. Int. Ed., vol. 50, 11769-11772, published Oct. 25, 2011, Supporting Information is attached) (Year: 2011).*

(Continued)

*Primary Examiner* — Shafiqul Haq
*Assistant Examiner* — Nam P Nguyen
(74) *Attorney, Agent, or Firm* — Karen A. LeCuyer; DeWitt LLP

(57) ABSTRACT

Described herein is cancer biomarker, e.g., a vesicle, capture surface that includes a substrate, a first plurality of nanoparticles attached to the substrate; a plurality of bifunctional tethers, wherein a first functionality of the bifunctional tethers is attached to at least a portion of the first plurality of nanoparticles; a second plurality of nanoparticles attached to a second functionality of at least a portion of the plurality of bifunctional tethers; a capture agent attached to at least a portion of the second plurality of nanoparticles; and a plurality of polymer brush molecules attached to the surface, (Continued)

wherein the polymer brush molecules have a lower molecular weight than the bifunctional tethers, and wherein the polymer brush molecules reduce nonspecific binding to the surface. Also described are method of capturing cancer biomarkers such as vesicles from a liquid biopsy sample.

11 Claims, 16 Drawing Sheets

(56) References Cited

U.S. PATENT DOCUMENTS

| | | |
|---|---|---|
| 2010/0184046 A1 | 7/2010 | Klass et al. |
| 2011/0039066 A1 | 2/2011 | Bauer et al. |
| 2012/0178638 A1 | 7/2012 | Damha et al. |
| 2016/0069861 A1 | 3/2016 | Santore et al. |
| 2016/0375143 A1 | 12/2016 | Gunatillake et al. |
| 2017/0001197 A1 | 1/2017 | He et al. |

FOREIGN PATENT DOCUMENTS

| | | | |
|---|---|---|---|
| WO | 2011045394 A1 | 4/2011 | |
| WO | 2013003624 A2 | 1/2013 | |
| WO | WO2013022995 A3 * | 2/2013 | ............... C12Q 1/68 |
| WO | 2015038493 A1 | 3/2015 | |
| WO | 2016183270 A1 | 11/2016 | |

OTHER PUBLICATIONS

Gao et al. ("Study of Streptavidin coated onto PAMAM dendrimer modified magnetite nanoparticle", Journal of Magnetism and Magnetic Materials, vol. 293, pp. 48-54, published 2005). (Year: 2005).*

Ding et al., "Synthetic strategies to enhance the long-term stability of polymer brush coatings", Journal of Materials Chemistry B, vol. 10, pp. 2430-2443, published 2022. (Year: 2022).*

Kizhakkedathu et al., "Poly(oligo(ethylene glycol)acrylamide) Brushes by Surface Initiated Polymerization: Effect of Macromonomer Chain Length on Brush Growth and Protein Adsorption from Blood Plasma", Langmuir, vol. 25, pp. 3794-3801, published Feb. 13, 2009. (Year: 2009).*

International Search Report and Written Opinion for International Application PCT/US2018/066400; International Filing Date: Dec. 19, 2018; dated Mar. 28, 2019; 10 pages.

Chen, Z. et al.; "Click synthesis of topological macromolecules"; Scientia Sinica Chimica, vol. 41, Issue No. 2; 2011; pp. 281-303; DOI: 10.1360/032010-759.

Feng, C. et al.; "Polymer Brushes: Efficient Synthesis and Applications"; Accounts of Chemical Research, vol. 51; 2018; pp. 2314-2323; DOI: 10.1021/acs.accounts.8b00307.

Hou, Z-L. et al.; "Self-assembly of Hyperbranched Polymer Cells"; Polymer Bulletin, vol. 9; 2015; pp. 9-20; DOI: 10.14028/j/cnki.1003-3726.2015.09.001.

Ozturk, K. et al.; "Effective targeting of gemcitabine to pancreatic cancer through PEG-cored Flt-1 antibody-conjugated dendrimers"; International Journal of Pharmaceutics, vol. 517; 2017; pp. 157-167; DOI: http://dx.doi.org/10.1016/j.ijpharm.2016.12.009.

Yamaguchi, H. et al.; "Dual-Labeled Near-Infrared/99mTc Imaging Probes Using PAMAM-Coated Silica Nanoparticles for the Imaging of HER2-Expressing Cancer Cells"; International Journal of Molecular Sciences, vol. 17, Issue No. 1086; 2016; 15 pages; DOI: 10.3390/ijms17071086.

* cited by examiner

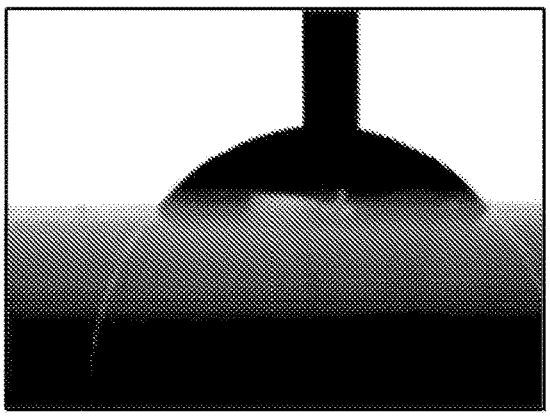
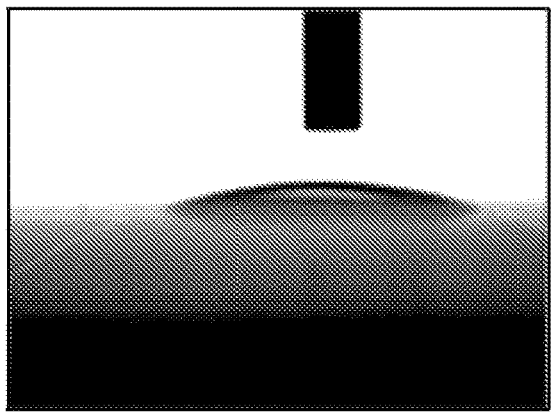
Fig. 5A  Fig. 5B
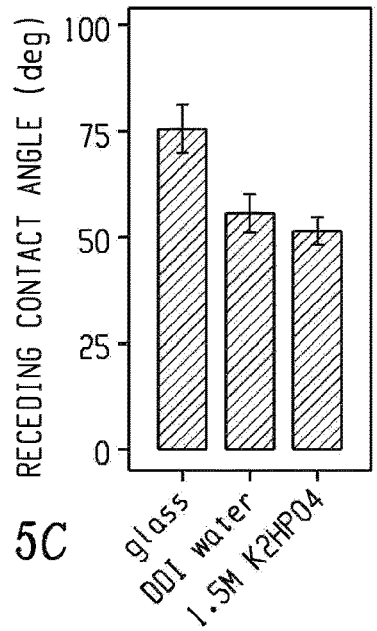
Fig. 5C
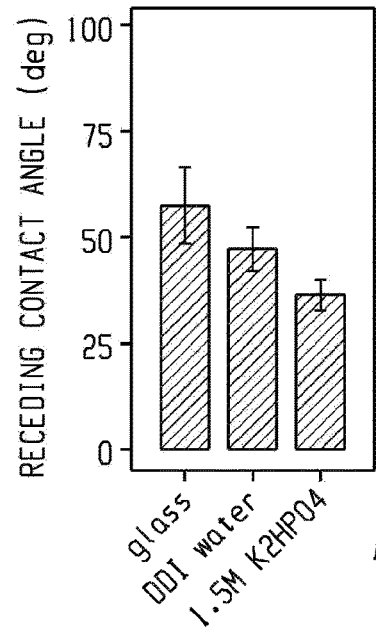
Fig. 5D
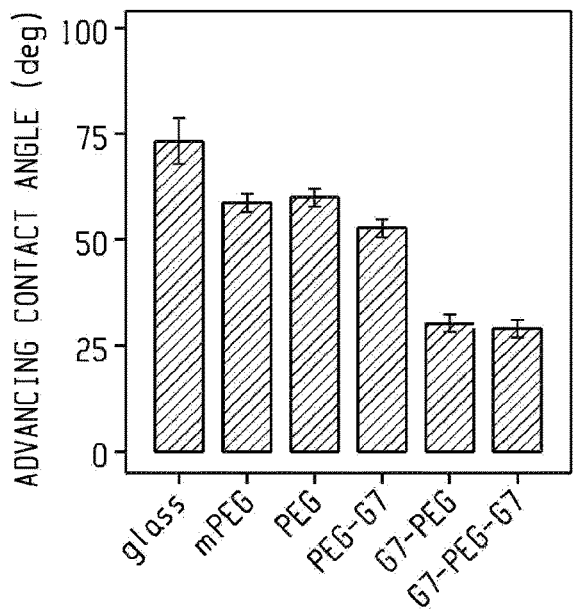
Fig. 5E

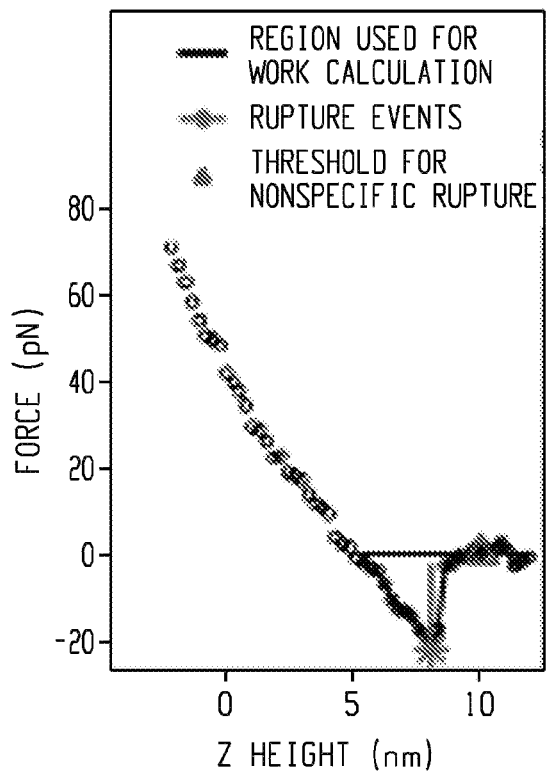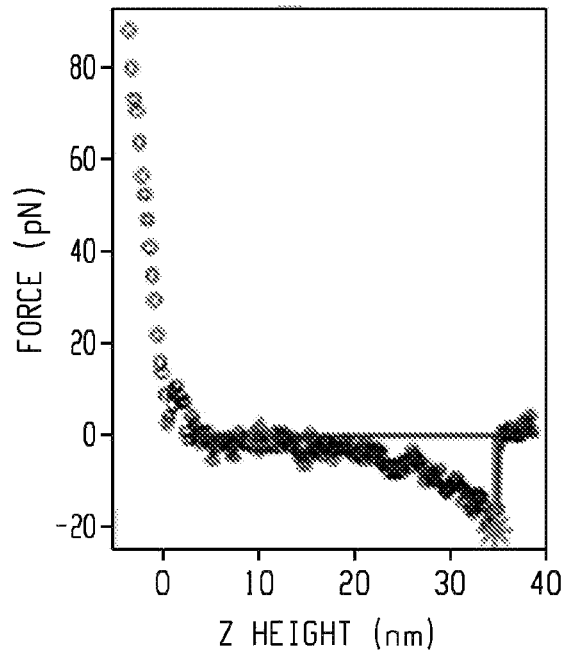
Fig. 12A    Fig. 12B
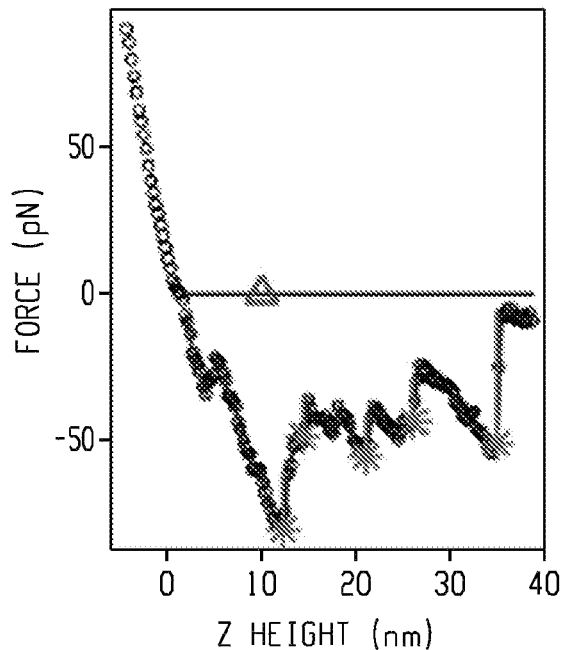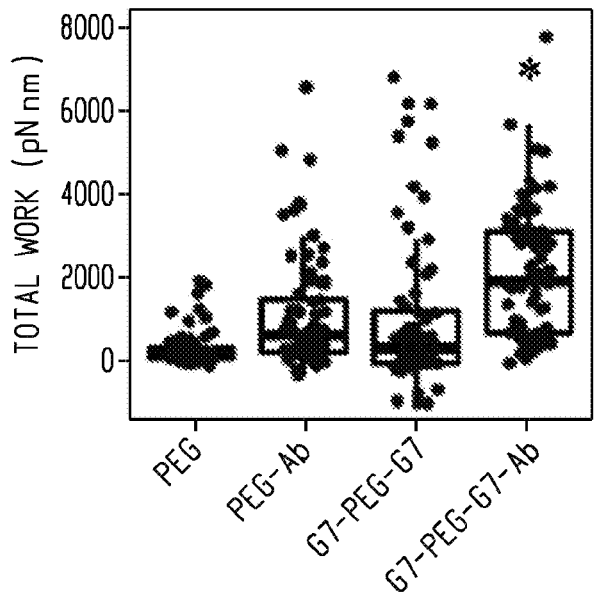
Fig. 12C    Fig. 12D

NANOENGINEERED SURFACES FOR CANCER BIOMARKER CAPTURE

CROSS REFERENCE TO RELATED APPLICATIONS

This application is a National Stage application of PCT/US2018/066400, filed Dec. 19, 2018, which claims the benefit of U.S. Provisional Application No. 62/609,481, filed Dec. 22, 2017, both of which are incorporated by reference in their entirety herein.

FIELD OF THE DISCLOSURE

The present disclosure is related to surfaces suitable for capture of cancer biomarkers such as vesicles, particularly exosomes, as well as methods of capturing cancer biomarkers.

BACKGROUND

Exosomes are nanoscale vesicles that transport functional ribonucleic acid (RNA) and protein between cells. The release rate and composition of exosomes from tumors into circulation has been linked to malignancy and metastasis. Exosomes are therefore a potentially rich source of information about the state of cancer, obtainable from a minimally invasive blood draw (called a "liquid biopsy"). Nevertheless, isolating and identifying exosome material is a challenge due to the small size and buoyancy of these vesicles.

Immunoaffinity separation techniques offer high selectivity, high sensitivity, and a lower likelihood of sample damage compared with the current gold standard of exosome separation by ultracentrifugation. Because exosome membranes are a mixture of intracellular and plasmalemma material, capture surfaces with antibodies against cancer cell surface markers are capable of separating subpopulations of tumor-derived vesicles. This enables quantification of relative release rates and increases purity for downstream assays like RNA sequencing. Immunoaffinity methods have been employed in microfluidic channels and on the surfaces of magnetic beads.

What is needed is an assay surface capable of isolating cancer biomarkers such as exosomes, for example from blood serum as part of a liquid biopsy.

BRIEF SUMMARY

In an aspect, a cancer biomarker capture surface comprises
a substrate,
a first plurality of nanoparticles attached to the substrate,
a plurality of bifunctional tethers, wherein a first functionality of the bifunctional tethers is attached to at least a portion of the first plurality of nanoparticles,
a second plurality of nanoparticles attached to a second functionality of at least a portion of the plurality of bifunctional tethers,
a capture agent attached to at least a portion of the second plurality of nanoparticles, and a plurality of polymer brush molecules attached to the surface, wherein the polymer brush molecules have a lower molecular weight than the bifunctional tethers, and wherein the polymer brush molecules reduce nonspecific binding to the surface.

In another aspect, a method of capturing a cancer biomarker from a liquid biopsy sample comprises
contacting the liquid biopsy sample with a cancer biomarker capture surface, the cancer biomarker capture surface comprising
a substrate,
a plurality of bifunctional tethers, wherein a first functionality of the bifunctional tethers is attached to the substrate, or optionally the first functionality of the bifunctional tethers is attached to at least a portion a first plurality of nanoparticles that are covalently attached to the substrate,
a second plurality of nanoparticles attached to a second functionality of at least a portion of the plurality of bifunctional tethers,
a capture agent attached to at least a portion of the second plurality of nanoparticles, and
a plurality of polymer brush molecules attached to the surface, wherein the polymer brush molecules have a lower molecular weight than the bifunctional tethers, and wherein the polymer brush molecules reduce nonspecific binding to the surface.

BRIEF DESCRIPTION OF THE DRAWINGS

FIG. 2a shows partial carboxylation of generation 7 (G7) poly(amidoamine) (PAMAM) dendrimer nanoparticles. FIG. 2b shows the preparation of PEG-G7 surfaces. FIG. 2c shows the preparation of G7-PEG-G7 surfaces.

FIG. 3a shows no increase in capture efficiency was observed for surfaces above 2 vol % of each tether.

FIG. 4a shows surfaces with G7 PAMAM dendrimers on the first layer (G7-PEG and G7-PEG-G7) significantly increase the hydrophilic behavior compared to other tested surfaces according to contact angle measurements. FIG. 4b shows a stylized rendering of nanoscale features on the G7-PEG-G7 surface imaged using AFM. FIG. 4c shows surfaces with two layers of G7 dendrimers (G7-PEG-G7) exhibit significantly higher roughness as measured using AFM. Bars show mean +/−standard deviation, * indicates p<0.05 of pairwise comparisons, while 'ns' indicates no statistical difference between groups.

FIGS. 5a-e show contact angle results. FIGS. 5a and b show images of water droplets at the time of collecting a) advancing and b) receding contact angle measurements. FIGS. 5c and d show the c) advancing and d) receding contact angles on glass are greater than mPEG controls, indicating successful conjugation of the polymers. A lower contact angle was observed when methoxy-terminated poly (ethylene glycol) (mPEG) was conjugated in a high salt buffer, indicating a denser brush. FIG. 5e shows advancing contact angle measurements complimentary to, and show the same statistical groupings. Charts show mean of n=8+/− standard deviation, capital letters in (e) indicate statistical groupings.

FIG. 6a epoxide-functionalized glass, FIG. 6b mPEG-coated glass, FIG. 6c glass coated with a mixture of mPEG and tethers, FIG. 6d surfaces with PEG-tethered G7, FIG. 6e surfaces coated with G7 before PEG tethers, and FIG. 6f G7-PEG-G7 capture surfaces. Scale bars represent 100 nm. Gray scale bars have a range of 12 nm.

FIG. 7 shows enhanced exosome binding to multilayered dendrimer surfaces.

FIG. 8a shows conjugation of full antibodies to carboxyl groups of a PEG-G7 surface.

FIGS. 12a-d shows quantification of adhesive energy using AFM force spectroscopy. Representative retraction curves from FIG. 12a unfunctionalized G7-PEG-G7, FIG. 12b antibody-functionalized PEG, and FIG. 12c antibody-functionalized G7-PEG-G7 surfaces showing single nonspecific rupture, single specific rupture, and five specific rupture events, respectively. Rupture events are indicated by * and vertical lines. The triangle separates adhesion defined as nonspecific (0-12 nm) vs. specific (>12 nm). The solid grey line delineates the values used to calculate work. FIG. 12d shows the total energy required to separate the probe from each capture surface. The * indicates p>0.5 compared to all other groups. Additional statistical groupings are omitted for clarity.

FIG. 15a shows separating a probe from nonfunctionalized G7-PEG-G7 surfaces required a statistically equivalent amount of nonspecific work as functionalized PEG-Ab surfaces. FIG. 15b shows beyond 12 nm, interactions were more likely to be specific between antibody and EpCAM. Work from the two capture surfaces, PEG-Ab and G7-PEG-Ab, were significantly greater than nonfunctionalized surfaces. Together, FIGS. 15a and b suggest that the high capture rates on G7-PEG-G7-Ab surfaces are due to both specific and nonspecific interactions. FIG. 15c shows rupture magnitudes showed no statistical trend depending on the surface, however, FIG. 15d shows that the rupture distance was significantly higher on functionalized surfaces compared to non-functionalized surfaces. Data show only curves with detected events. Capital letters indicate statistically significant groupings.

Figure 1:
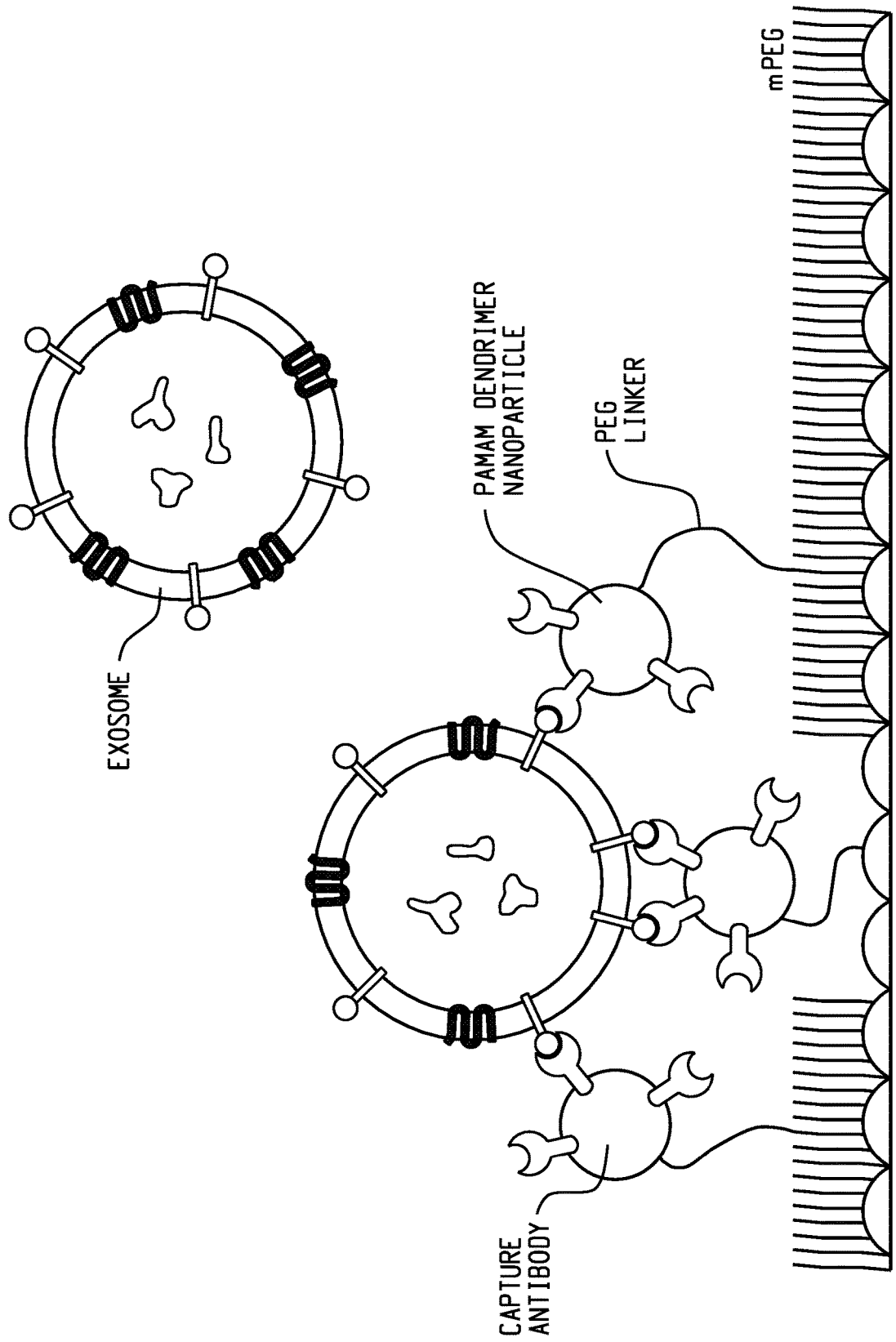
FIG. 1 is a schematic of a surface of the present disclosure. Nanoparticle-mediated multivalent binding, in conjunction with variable-length tethers, enables multiple antibodies to bind to cancer biomarkers such as exosomes on the order of 20-200 nm in diameter.

The above-described and other features will be appreciated and understood by those skilled in the art from the following detailed description, drawings, and appended claims.

DETAILED DESCRIPTION

As described herein, the inventors have used immunoaffinity methods combined with capture surfaces to demonstrate the capture of cancer biomarkers such as exosomes from liquid biopsies. The sensitivity and selectivity of immunoaffinity capture methods are enhanced when multiple antibody molecules are able to interact with the analyte because multivalent binding dramatically lowers the dissociation rate. Previously, methods were developed for the capture of circulating tumor cells (CTCs) using polyamidoamine dendrimer nanoparticles. These hyperbranched polymers facilitated multivalent binding in two ways: a high density of functional groups allows for multiple antibody molecules to be conjugated to each approximately 9 nm diameter nanoparticle, and the branched structure allows for flexibility in the orientation of binding domains. CTCs, however, are 50-1,000 times larger in diameter than exosomes. Thus it was unknown if similar surfaces could also be used to capture cancer biomarkers such as exosomes.

Specifically, described herein are surfaces and devices for capture of cancer biomarkers such as cancer-derived vesicles, including exosomes, particularly from blood samples, and more particularly from plasma. Cells and vesicles that are shed from tumors contain a wealth of information about the cancer, including its susceptibility to specific drugs and its potential for metastasis. A major challenge for such a "liquid biopsy" is the identification and separation of tumor-derived material from whole blood. Described herein are surfaces and devices with multivalent binding to trap cancer biomarkers with high efficiency and specificity. The surfaces unexpectedly achieve multivalent binding on the small scale of vesicles, which can range from 20-200 nm in diameter, by using a densely-packed network of antibody-coated nanoparticles attached to a substrate surface with flexible tethers. An effective liquid biopsy containing cancer biomarkers such as tumor-derived vesicles has the potential to provide a cancer diagnosis earlier than other methods, detect metastasis, and guide personalized therapies based on changes in gene expression.

Liquid biopsies are an emerging, non-invasive technique for cancer diagnosis. Because the information is collected in a blood draw, a liquid biopsy can potentially be used detect cancer earlier than conventional techniques. In addition, liquid biopsies can provide information about tumors that are too small or inaccessible to be sampled by conventional biopsy techniques, and can be used multiple times over the course of cancer treatment.

Tumor-shed material, e.g., cancer biomarkers, includes nucleic acids (e.g., DNA), proteins, vesicles, and whole cells.

Cancerous vesicles, which include exosomes, contain a mixture of materials from the cell packaged inside material drawn from both intracellular and extracellular membranes. These vesicles are recognized as a major intercellular communication pathway, and have recently been implicated in inducing metastatic behavior in cancer cells and pre-metastatic niche formation. Vesicle payloads include mRNA and small RNAs that reflect gene expression patterns, and may signal changes of drug resistance or susceptibility in the course of cancer treatment. Of particular importance, healthy blood serum contains $10^{12}$ exosomes $ml^{-1}$, carrying 0.2-2.5 ng $ml^{-1}$ of RNA, which can be assayed.

The tumor-shed vesicles themselves are small. Exosomes, for example, which are vesicles used for intercellular communication, range from 20-200 nm in diameter. The most common methods of exosome isolation are ultracentrifugation, which separates material by buoyancy and requires hours to run, or gradient centrifugation, which contaminates collected material by coating them with polymers. Exosomes contain portions of the plasmalemma and can therefore be identified by the same surface markers expressed by their originating cells. Exosomes are further distinguishable from other vesicles by the presence of transmembrane proteins from the endothelial reticulum. Emerging methods to efficiently isolate exosomes from whole blood rely, at least in part, on antibody recognition of these membrane proteins.

Separation of cancer-derived exosomes from non-cancerous material requires immunological techniques. This is true even when exosomes are successfully separated from other blood components by centrifugation or other methods. Separation relies upon antibodies, which are naturally produced by the immune system to recognize foreign material but can also be manufactured to recognize and bind to many other proteins. Antibodies form the basis for many techniques in both basic science and medical diagnosis.

While all exosomes express intracellular proteins like tetraspanins (notably CD63), cancerous cell vesicles can be differentiated from white blood cell-derived vesicles and other material by the presence of specific transmembrane proteins. For instance, antibodies that specifically bind epithelial cell adhesion molecule (EpCAM) and epidermal growth factor receptors (EGFR and HER2) can be used to separate breast cancer cells from leukocytes and other white blood cells. Antibodies against proteins that are overexpressed in target material are conjugated to solid supports or other easily-separated media like magnetic beads.

Advantageously, the surfaces and devices described herein can include a cocktail of antibodies or other capture agents chosen and tuned to specifically recognize vesicles shed by specific types of cancer. The nanoengineered surface is designed to take advantage of multivalent binding, which provides two benefits. First, recognition of a vesicle by multiple different antibody molecules increases specificity for the cancer of interest. Second, multiple binding events exponentially increase the energy of binding, resulting in higher capture efficiency. FIG. 1 shows a schematic of multivalent binding of exosomes to a capture surface.

In an aspect, a cancer biomarker capture surface comprises
a substrate,
a first plurality of nanoparticles attached to the substrate,
a plurality of bifunctional tethers, wherein a first functionality of the bifunctional tethers is attached to at least a portion of the first plurality of nanoparticles,
a second plurality of nanoparticles attached to a second functionality of at least a portion of the plurality of bifunctional tethers,
a capture agent attached to at least a portion of the second plurality of nanoparticles, and
a plurality of polymer brush molecules attached to the surface, wherein the polymer brush molecules have a lower molecular weight than the bifunctional tethers, and wherein the polymer brush molecules reduce nonspecific binding to the surface.

In certain embodiments, the tethers can be attached to the surface in the absence of the first plurality of nanoparticles, that is, the first plurality of nanoparticles is omitted from the surface.

Exemplary cancer biomarkers include circulating tumor cells, vesicles, proteins, and DNA. A specific cancer biomarker is a vesicle such as an exosome.

Exemplary substrates include glass substrates, specifically functionalized glass substrates. Other surfaces which can be used as substrates include polymers (e.g., polymethylmethacrylate, polycarbonates, and cyclic olefin polymers) and silicone (silicone wafers and poly(dimethylsiloxane)s (PDMS)). Exemplary functional groups for the substrate surfaces include an epoxy group, a carboxyl group, a thiol group, an alkyne group, an azide group, a maleimide group, a hydroxyl group, an amine group, an aldehyde group, or a combination comprising at least one of the foregoing. A specific substrate is epoxy-functionalized glass such as SuperEpoxy®, ArrayIt Inc, Sunnyvale, Calif.

Figures 2A, 2B, 2C:
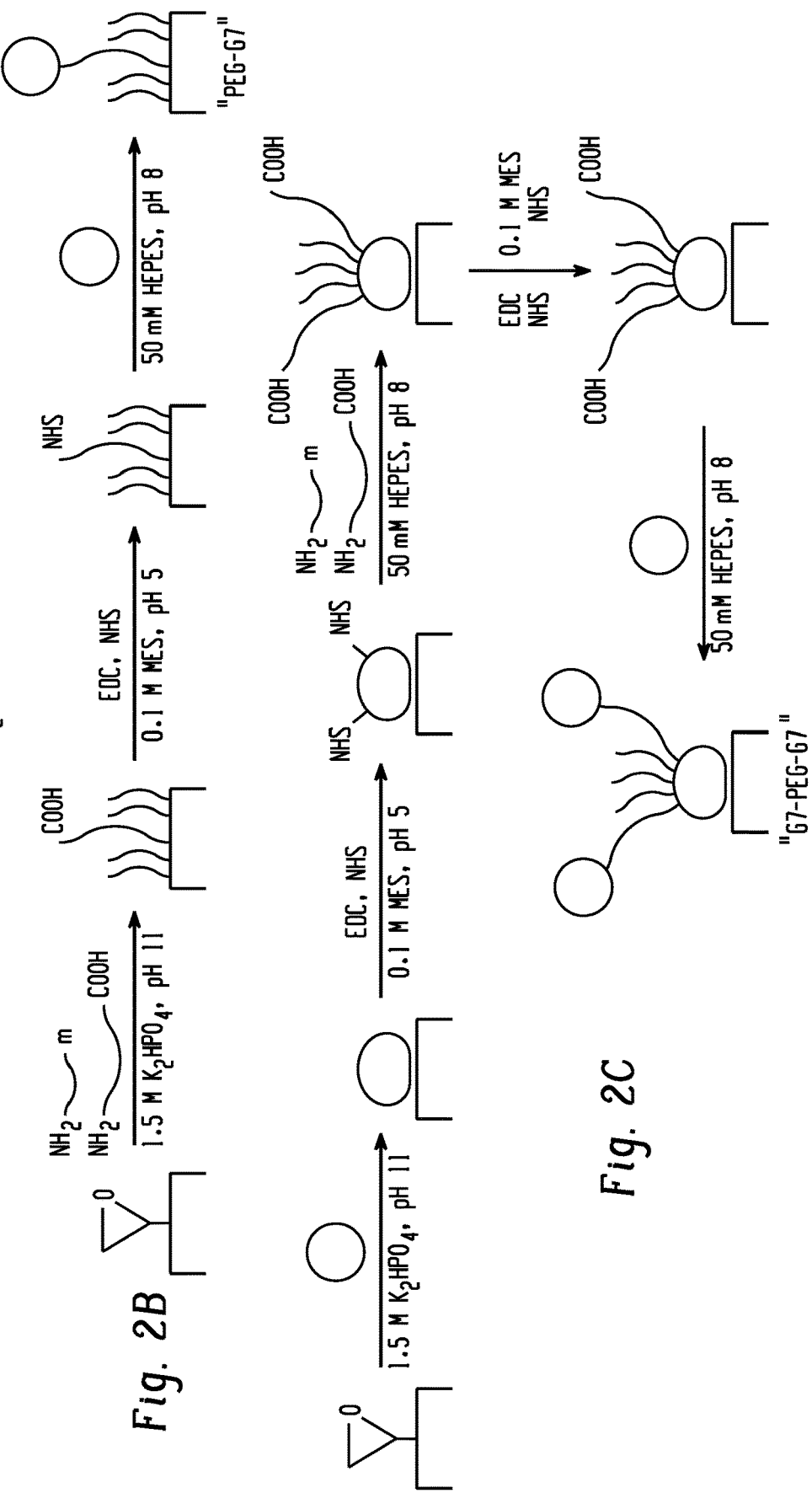
FIGS. 2a-c are a summary of polymer surface preparation.

The first plurality of nanoparticles is attached to the substrate, for example, by reacting functional groups on the nanoparticles with the functional groups on the substrate. The first plurality of nanoparticles can be attached to the substrate by covalent or noncovalent, specifically covalent bonds. For example, when an epoxy-functionalized substrate is employed, nanoparticles functionalized with primary amine groups may be attached to the surface by reaction of the surface epoxy groups with primary amine groups on the nanoparticles. The attached first plurality of nanoparticles can be modified to provide a second functionality, such as an N-hydroxysuccinimide (NETS) functionality, which can then react with a functional group on the first end of the bifunctional tether, such as with an amine group on the first end of the bifunctional tether. The unbound end of the bifunctional tether can then be modified to provide a second functionality, such as an NETS functionality, which can then react with a functional group on the second plurality of nanoparticles, for example, nanoparticles functionalized with primary amine groups. Finally, a portion of the unreacted carboxyl groups on the second plurality of nanoparticles can be modified to provide an NETS functionality, for example, which can then react with the capture agent to provide the capture surface. (See, FIG. 2c) Other surface chemistries using carboxylic acids, thiols, hydroxyl groups, epoxides, azide groups, alkynes, isothiocyanides, and acrylates can be applied.

In an embodiment, the first plurality of nanoparticles and the second plurality of nanoparticles both comprise either the same or a different dendritic polymer. Dendritic polymers include a dendrimer, a dendritic star-branched polymer, a dendritic hyperbranched polymer, a dense dendritic star-branched polymer, a hypercomb-branched dendritic polymer, or a combination comprising at least one of the foregoing. A dendritic polymer includes several layers or generations of repeating units, usually referred to as branch cells, which all contain one or more branch points. Dendrimers comprise a plurality of dendrons that emanate from a common core which can be a single atom or a group of atoms. Each dendron generally includes terminal surface groups, interior branch junctures having branching functionalities greater than or equal to two, and divalent connectors that covalently connect neighboring branching junctures. Dendritic star-branched polymers having a plurality of arms emanating from a nucleus. Hyperbranched dendrimers have very large numbers of branches and can have imperfectly branched or irregular structures. Methods of preparing and characterizing dendrimers, dendrons, hyperbranched polymers, star-branched polymers, dense star-branched polymers and hypercomb-branched polymers are all well known in the art and thoroughly described in the literature More specifically, the first plurality of nanoparticles and the second plurality of nanoparticles comprise the same or a different poly(amidoamine) dendrimer. Poly(amidoamine) dendrimers can comprise a generation 3 PAMAM dendrimer, a generation 4 PAMAM dendrimer, a generation 5 PAMAM dendrimer, a generation 6 PAMAM dendrimer, a generation 7 PAMAM dendrimer, a generation 8 PAMAM dendrimer, a generation 9 PAMAM dendrimer, or a combination comprising at least one of the foregoing.

A first functionality of the bifunctional tethers is attached to at least a portion of the first plurality of nanoparticles. Attaching includes covalent or noncovalent, specifically covalent attachment.

In an embodiment, the bifunctional tethers comprise a poly(ethylene glycol) or other non-fouling polymers and peptides. Poly(ethylene glycol) has the formula H—(O—$CH_2$—$CH_2$)n-OH, wherein n is preferably 10-500. Exemplary non-fouling polymers and peptides include poly(oxazoline), propylene suloxide, polyglycerol dendrons, dextran, polybetaines, and hydrophilic, uncharged, alpha-helical-forming polypeptides.

In an embodiment, the plurality of bifunctional tethers comprises a mixture of low molecular weight tethers and high molecular weight tethers, wherein the low molecular weight tethers have a molecular weight of 300 to 5000 Da, and the high molecular weight tethers have a molecular weight of 5000 to 100,000 Da. The ratio of low molecular weight tethers to high molecular weight tethers can be 0:20 wt/wt to 20:0 wt/wt. Advantageously, the use of a mixture of low molecular weight tethers and high molecular weight tethers can improve multivalent binding by allowing more binding sites to wrap around the vesicle compared to low molecular weight tethers alone (See, e.g., FIG. 1).

The capture surface includes a plurality of polymer brush molecules attached to the surface, wherein the polymer brush molecules have a lower molecular weight than the bifunctional tethers, and wherein the polymer brush molecules reduce nonspecific binding to the surface. Exemplary polymer brush molecules include methoxy polyethylene glycol having a molecular weight of 300 to 5000 Da, specifically 2000 Da, so long as the polymer brush molecules have a lower molecular weight than the low molecular weight tethers.

A second plurality of nanoparticles is attached to a second functionality of at least a portion of the plurality of bifunctional tethers. The second plurality of nanoparticles can be covalently or noncovalently attached, specifically covalently attached. The first and second plurality of nanoparticles can be the same or different.

Attached to at least a portion of the second plurality of nanoparticles is a capture agent for the cancer biomarker to be captured. The capture agent can be covalently or noncovalently, specifically covalently, attached. Exemplary capture agents include an antibody, a partially reduced antibody, an antibody fragment, a recombinant protein, a peptide, an aptamer, a small molecule, or a combination comprising at least one of the foregoing.

The term "antibody" includes (i) an intact antibody (for example, a monoclonal antibody or polyclonal antibody), ii) partially reduced antibodies that are treated with a reducing agent to cleave at least a portion of the disulfide bonds connecting the two halves of the antibody, iii) half-antibodies, each with a single binding domain, (iv) antigen binding portions thereof, including, for example, an Fab fragment, an Fab' fragment, an (Fab')$_2$ fragment, an Fv fragment, a single chain antibody binding site, an sFv, (v) bi-specific antibodies and antigen binding portions thereof, and (vi) multi-specific antibodies and antigen binding portions thereof.

Exemplary antibodies include Trastuzumab (Herceptin®), Bevacizumab (Avastin®), anti-CD33 antibody (Mylotarg®), anti-CD20 antibodies (Zevalin® and Bexxar®), and their fragments and engineered forms (e.g., diabody, avimer, etc.).

In an embodiment, the capture agent specifically binds an exosome surface marker. Exemplary exosome surface markers include CD63, CD81, CD9, or a combination comprising at least one of the foregoing.

In an embodiment, the capture agent specifically binds an exosome surface marker for an epithelial cancer-derived exosome, such as EpCAM, EGFR, HER2, cadherin 11, PDL1, or a combination comprising at least one of the foregoing. Epithelial cell adhesion molecule (EpCAM) is frequently overexpressed by a variety of carcinomas such as lung, colorectal, breast, prostate, head and neck, and hepatic origin, but is absent from hematologic cells. Anti-EpCAM antibody is commercially available from several sources including, for example, R&D Systems, Abcam, and Millipore. Alternatively, anti-EpCAM antibodies useful for practicing the methods of the disclosure or generating the devices of the disclosure can be generated by any method known in the art.

In another embodiment, the exosome surface marker comprises the prostate cancer marker PSA or the melanoma marker CD146.

Capture agents can be surface immobilized in patterns and in mixtures of capture agents, for example. A patterned slide can separately capture and immobilize exosomes derived from different sources based on their surface markers. Patterned surfaces separately capture and immobilize exosomes derived from different sources based on their surface markers. For example, epithelial-derived exosomes can be separated from mesenchymal-derived exosomes and separately quantified and sampled. Such surfaces would test for multiple number of disease states on a single slide. Patterned slides can be fabricated using physical masks, stamping, inkjet printing, microarray spotting, and other methods, either by patterning the polymer layers or the capture antibodies. The patterned glass slides can be prepared using soft lithography. For example, PDMS gaskets can be used to mask unpatterned areas of the glass and define the separate capture domains. Each capture domain can be treated with a different mixture of capture agents. The silicone gasket can be peeled off and the entire surface treated with the polymer brush.

In another embodiment, the multiple capture agents can be surface immobilized after being mixed each other, creating the surfaces without patterns.

Also included herein is a device comprising the vesicle capture surface described herein, for example, a microfluidic device. Exemplary microfluidic devices can include a channel that includes the vesicle capture surface. The channel can have any suitable cross-sectional shape. For example, the channel can be rectangular, triangular, circular, or elliptical. The channel can have a height of about 50 µm to about 600 µm, about 100 µm to about 500 µm, about 200 µm to about 400 µm. Other suitable heights include, for example, about 50, 100, 150, 200, 250, 300, 350, 400, 450, 500, 550, or 600 µm. The channel can have a width of about 200 µm to about 2000 µm, about 400 µm to about 1500 µm, about 500 µm to about 1000 µm, or about 600 µm to about 800 µm. Other suitable widths include, for example, about 200, 300, 400, 500, 600, 700, 800, 900, 1000, 1100, 1200, 1500, 1600, 1700, 1800, 1900, or 2000 µm. The channel can have a length of about 200 µm to about 5000 µm, about 400 µm to about 4000 µm, about 600 µm to about 2000 µm, or about 800 µm to about 1000 µm. Other suitable lengths include, for example, about 200, 300, 400, 500, 600, 700, 800, 900, 1000, 1500, 2000, 2500, 3000, 3500, 4000, 4500, or 5000 µm.

A method of capturing a cancer biomarker, e.g., a cancer vesicle, from a liquid biopsy sample comprises contacting the liquid biopsy sample with a cancer biomarker capture surface, the vesicle capture surface comprising a plurality of bifunctional tethers, wherein a first functionality of the bifunctional tethers is attached to the substrate, or optionally the first functionality of the bifunctional tethers is attached to at least a portion a first plurality of nanoparticles that are covalently attached to the substrate, a second plurality of nanoparticles attached to a second functionality of at least a portion of the plurality of bifunctional tethers, a capture agent attached to at least a portion of the second plurality of nanoparticles, and a plurality of polymer brush molecules attached to the surface, wherein the polymer brush molecules have a lower molecular weight than the bifunctional tethers, and wherein the polymer brush molecules reduce nonspecific binding to the surface.

In an embodiment, the liquid biopsy sample is a plasma sample. Buffy coat samples which include CTCs must be analyzed within a day. Advantageously, plasma samples can be stored long-term, allowing for multiple rounds of analysis on the same sample.

Contacting the liquid biopsy sample with the vesicle capture surface can be done under a static condition or under flow conditions by methods known in the art. Flow conditions include microfluidic and microfluidic flow conditions. Under flow conditions, the vesicle capture surface can be a part of a device comprising a flow chamber and/or a syringe filter.

Once the cancer biomarker such as cancer vesicles, e.g., exosomes, have been captured on the surface, the contents can be released with a mild detergent wash and analyzed. Analysis of the vesicles can include RNA sequence analysis by methods known in the art. For example, vesicles can be lysed and the RNA retrieved for RT-PCR analysis.

Methods to determine the mRNA level of a gene in a sample are well known in the art. For example, in some embodiments, the mRNA level can be determined by Polymerase Chain Reaction (PCR), qPCR, qRT-PCR, RNA-seq, microarray analysis, SAGE, MassARRAY technique, next-generation sequencing, or FISH.

Alternatively, the captured exosome, either on the capture surface, or released from the capture surface, can be analyzed using immunocytochemical and other fluorescent imaging techniques. In another embodiment, tethers attached to gold-coated prism glass surfaces via sulfhydryl chemistry are compatible with highly sensitive plasmonic resonance detection that is increasingly used as a label-free method for exosome detection.

The results of RNA sequence analysis, for example, can be used to guide treatment of the subject. For example, the methods described herein can be used to monitor disease progression. Such monitoring can take place before, during or after treatment of cancer by surgery or therapy. Thus, in one aspect the present method includes monitoring the progression of cancer in a subject. Serial measurements can allow an assessment of whether or not, or the extent to which, the cancer is worsening, thus, for example, allowing a more reasoned decision to be made as to whether therapeutic intervention is necessary or advisable.

Monitoring can also be carried out, for example, in an individual who is thought to be at risk of developing cancer, in order to obtain an early, and ideally pre-clinical, indication of cancer. In this way, the methods can be carried out on "healthy" patients (subjects) or at least patients (subjects) which are not manifesting any clinical symptoms of cancer, for example, patients with very early or pre-clinical stage cancer, e.g., patients where the primary tumor is so small that it cannot be assessed or detected or patients in which cells are undergoing pre-cancerous changes associated with cancer but have not yet become malignant.

The present methods provide for predicting the response of a subject to therapy. In such methods the choice of therapy may be guided by knowledge of the level in the sample of an expression product (or related metabolite) of one or more genes.

The present methods also include a method of determining (or monitoring) the efficacy of a therapeutic regime being used to treat cancer. In such methods, an alteration (increase or decrease) in the level of an expression product (or related metabolite) of one or more genes indicates the efficacy of the therapeutic regime being used.

The present methods also include a method for detecting the recurrence of cancer.

The invention is further illustrated by the following non-limiting examples.

EXAMPLES

Methods

Materials: Generation 7 (G7) PAMAM dendrimers were obtained from Dendritech (Midland, Mich.) and all polyethylene glycol (PEG) was obtained from JenKem (Plano, Tex.). Epoxide-functionalized glass surfaces were in the form of standard microscope slides from Tekdon (Myakka City, Fla.) or within 96 well plates from Arrayit (Sunnyvale, Calif.). Fiberglass pre-filters were purchased from Millipore (Cork, Ireland).

All capture antibodies and recombinant EpCAM were obtained from R&D Systems (Minneapolis, Minn.), while the ELISA secondary detection enzyme and substrate were obtained from Santa Cruz Biotechnology (Dallas, Tex.). Sharp silicon nitride probes for imaging (SNL) and gold-coated silicon nitride probes for force spectroscopy (NPG) were obtained from Bruker Probes (Camarillo, Calif.). The bincinchonininic acid (BCA) protein assay and Qubit® high sensitivity RNA assay were obtained from Thermo Fisher Scientific (Waltham, Mass.). The SMCC crosslinker was supplied by CalBioChem (San Diego, Calif.), and all other reagents were supplied by Sigma Aldrich (St. Louis, Mo.).

Nanoparticle Carboxylation: G7 PAMAM dendrimers was partially carboxylated by reacting 1 mg with 0.308 mg succinic anhydride in 2 ml dimethyl sulfoxide (DMSO) overnight (FIG. 2a), then purified in double distilled water with a 10,000 molecular weight cutoff centrifugal filter (Amicon) and lyophilized. The extent of carboxylation was verified to be between 60 and 70% by NMR spectroscopy. The acronym "G7" refers to these partially-carboxylated nanoparticles.

Surface Preparation: Fiber glass prefilters were cleaned and treated in 2 vol. % (3-glycidyloxypropyl)trimethoxysilane in 95 vol. % ethanol and 0.1 vol. % acetic acid for 90 min, rinsed with ethanol, and baked overnight at 120° C. to introduce epoxide groups. All other surfaces were created on epoxy-functionalized glass-bottom, black-walled 96 well plates (Arrayit) or glass slides (Tekdon). To confine surface treatments on slides, silicone gaskets were cast from polydimethylsiloxane and wells were created using a 10 mm biopsy punch.

For G7-PEG-G7 surfaces (FIG. 2c), epoxide-functionalized glass was treated overnight with 0.1 mg/ml G7 in 1.5 M potassium phosphate, pH 11. The surfaces were rinsed and activated for 1 h with 15 mM 1-ethyl-3-(3-dimethylaminopropyl)carbodiimide hydrochloride (EDC) and 25 mM N-hydroxysuccinimide (NETS) in 100 mM 2-(N-morpholino)ethanesulfonic acid buffer (YMS), pH 5, with 150 mM sodium chloride before treating with 0.5 mg/ml PEG for 2 h. Unless otherwise noted, the PEG solution consisted of 0.48 mg/ml 2000 Da methoxy-PEG-amine, 0.01 mg/ml 5000 Da carboxy-PEG-amine, and 0.01 mg/ml 20,000 Da carboxy-PEG-amine in 50 mM 4-(2-hydroxyethyl)-1-piperazineethanesulfonic acid buffer with 150 mM sodium chloride (HBSS), pH 8. Other surfaces were prepared similarly, with the initial polymer mixture in 1.5 M potassium phosphate to encourage precipitation on the glass surface. Note that in experiments comparing SMCC-conjugated antibodies, amine-PEG-amine tethers were used in place of carboxy-PEG amine. All surfaces were rinsed with Tris-buffered saline containing 0.1 vol. % Tween® 20 (TBST) to block hydrophobic pockets and unreacted epoxide groups.

Bead Binding Assays: The binding capacities of various surfaces prepared in microplates were compared by incubation with protein-coated beads in a pilot experiment to determine the minimum sufficient PEG tether concentration. Surfaces were prepared with mixtures of 5000 MW carboxy-PEG-amine and 20,000 MW carboxy-PEG-amine ranging from 0 to 20 vol. % at 0.5 mg ml$^{-1}$, with the balance made up by 2,000 MW methoxy-PEG-amine. The PEG-PAMAM surfaces were functionalized with anti-EpCAM according to the methods described below. Carboxy-functionalized, yellow-green fluorescent, 0.2 μm polystyrene beads (Thermo Fisher FluoSpheres®) were activated with EDC and NHS for 30 min, centrifuged at 16,000×g for 30 min, and resuspended in 1 μg ml$^{-1}$ recombinant EpCAM-Fc overnight. Unconjugated protein was removed by another centrifugation, and the beads were resuspended in 1 wt % bovine serum albumin (BSA, Sigma Aldrich) in PBS.

Figure 3A:
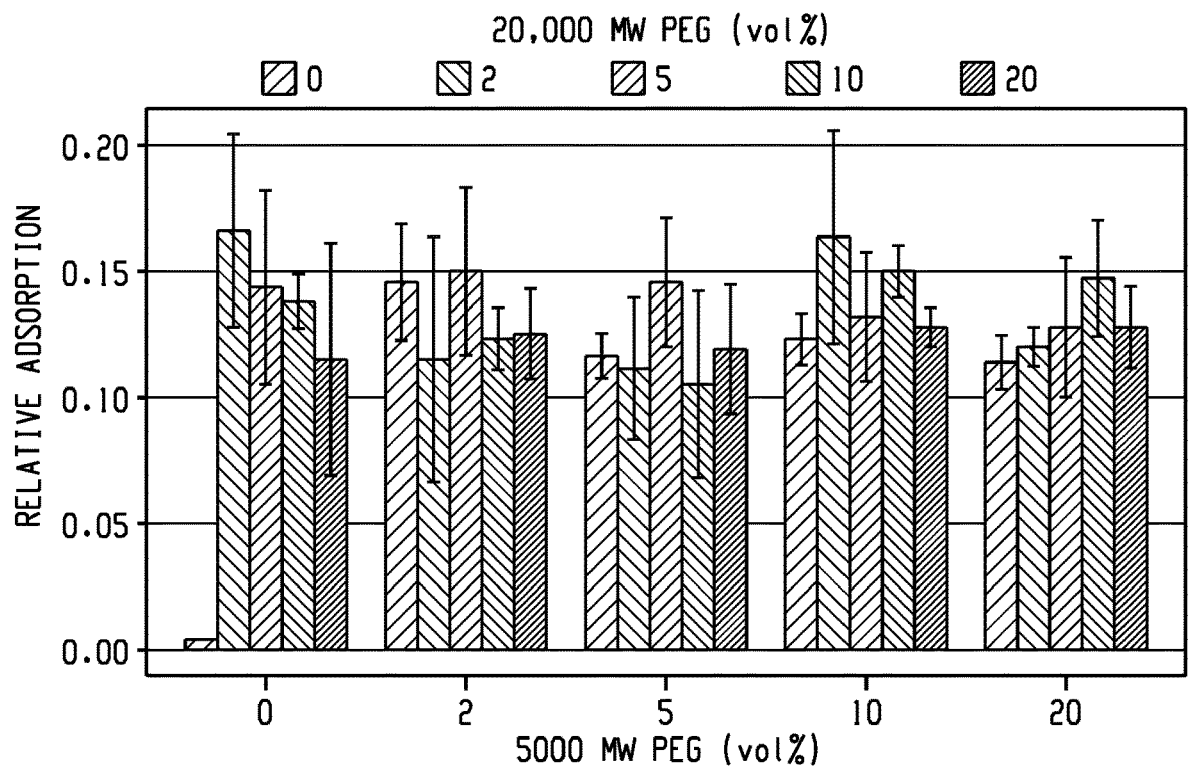
FIGS. 3a and b show pilot experiments to determine minimal PEG tether concentrations sufficient for capturing 200 nm functionalized beads.
Figure 3B:
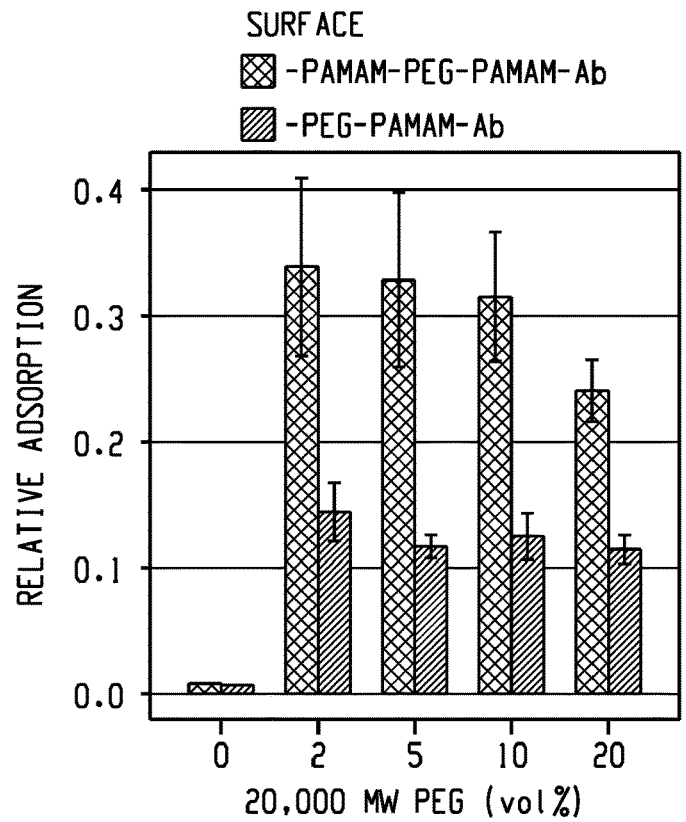
FIG. 3b shows G7 dendrimer pre-coating (G7-PEG-G7) significantly enhanced capture compared to PEG-G7.

A comparison of PEG-G7 surfaces showed no difference in capture efficiency above 2 vol % of each tether (FIG. 3a), corresponding to 2 μM 5000 MW, 0.5 μM 20,000 MW, and 240 μM 2000 MW methoxyPEG. The bead assay further confirmed higher rates of adsorption on G7-PEG-G7 surfaces compared with PEG-G7 (FIG. 3b).

Contact Angle Measurements: Advancing and receding contact angles on modified slides were recorded with a Dataphysics OCA 15 Plus device with SCA 20 software (Filderstadt, Germany) using the sessile drop method. Measurements were collected using 8 μl droplets of double distilled water (DDI) ejected at 1 μl s$^{-1}$.

The sessile drop contact angle technique was used to quantify the relative hydrophilicity of various prepared surfaces and verify polymer conjugation. The contact angles refer to the angle between the droplet-air and droplet-surfaces interfaces after the droplet was ejected (advancing, FIG. 5a) and after the majority of the droplet was retracted (receding, FIG. 5b). Measurements were used to verify enhanced conjugation of mPEG in a high-salt buffer compared to DDI water (FIG. 5c,d). FIG. 5e shows the advancing contact angle results that complement receding contact angle measurements.

Roughness Measurements: Height profiles for roughness quantification were collected from polymer-modified slides with sharp, silicon nitride probes (Bruker SNL) using an Asylum Infinity™ Bio system (Oxford Instruments, Santa Barbara, Calif.). Measurements of samples hydrated with phosphate buffered saline (PBS) were collected in tapping (AC) mode. Roughness was quantified as the Rq value (root mean square) of a 500×500 nm$^2$ image. Representative height scans are shown in FIG. 6.

Protein Quantification Assay: Microplates were functionalized with anti-CD63 and treated with filtered human serum for 2 h as with the ELISA test, above. After three PBS rinses, the protein content remaining in the well was quantified by bicinchoninic assay kit (microBCA™, Thermo Fisher) with 2 h incubation at 37° C. Protein was quantified using a BSA standard curve.

Antibody Functionalization: Two conjugation methods were evaluated: attachment of full antibodies via NHS to carboxyl groups on polymers, and attachment of partially-reduced antibodies via SMCC to amine groups on polymers. For full antibodies, surfaces were incubated with 15 mM EDC and 25 mM NHS in IVIES buffer for 30 min before incubation with capture antibodies in HBSS (Hank's Salt) for 4 h at room temperature or overnight at 4° C. Partially reduced antibodies were treated for 30 min with 3 mg ml$^{-1}$ cysteamine HCl at 37° C. in PBS supplemented with 5 mM ethylenediaminetetraacetic acid (EDTA), then purified using centrifugal filtration and a 3000 MWCO filter (Amicon). Surfaces were incubated under 0.5 mg ml$^{-1}$ water-soluble SMCC in PBS with EDTA for 30 min before rinsing and adding antibodies. Antibody incubations were 10 μg ml$^{-1}$. Both procedures are summarized in FIG. 8.

Antibody Density Quantification: Human immunoglobulin G (IgG, Sigma-Aldrich) was dissolved in HBSS at 10 mg/ml. AlexaFluor™405-NHS (Thermo Fisher) was dissolved in DMSO at 1 mg/ml and added, 10 μl at a time, to the IgG mixture to a final molar ratio of 4:1. The mixture was incubated overnight at 4° C. before diluting in PBS, separating by centrifugal filtration (10,000 MWCO, Amicon), and resuspending in PBS with 5 mM EDTA. The labeled IgG was reduced with cysteamine and conjugated to functionalized microplates as described above. The fluorescence signal with 400 nm excitation, 430 nm emission was quantified using a Synergy™ microplate reader (Biotek) and normalized to a standard curve of unconjugated protein. Binding site density was calculated assuming a molecular weight of 150 kDa and two functional binding sites per non-reduced molecule. The conjugation density of full antibodies as in FIG. S5a was not quantified, as the amine-reactive fluorophore blocked reactive groups.

ELISA Assay: Human serum (Sigma-Aldrich) was vacuum-filtered through a 0.22 µm polyethersulfone membrane (EMD Millipore) and incubated in a microplate functionalized with anti-CD63 (R&D Systems MAB5048) for 2 h under gentile agitation at 200 µl/well. Microplates were rinsed and fixed overnight in 4% paraformaldehyde at 4° C. The plates were blocked with 1 wt % BSA, rinsed with TB ST, and incubated 90 min under mouse anti-human CD81 (Santa Cruz 166028) diluted 1:200 in PBS. The plates were then incubated for 90 min under horseradish peroxidase-conjugated goat anti-mouse (Santa Cruz 2031), rinsed, and developed with 1.6 mg/ml o-phenylenediamine (Santa Cruz) and 1.6 vol. % concentrated hydrogen peroxide (Aqua Solutions) in 100 mM sodium phosphate dibasic and 50 mM citrate buffer, pH 5, for 15 min. Absorbance at 492 nm was quantified by microplate reader.

To supplement pilot studies with beads establishing sufficient PEG tether concentrations, additional ELISA assays were performed to compare 2 vol % PEG tethers to 10× the amount reported in the main text. Consistent with bead binding assays, there was no difference due to tether concentration (data not shown).

Exosome Culture, Isolation, and Western Blotting: The human metastatic breast cancer line MDA-MB-231 (ATCC, Manassas, Va.) was expanded in L15 Medium (Corning, Tewksbury, Mass.) supplemented with 10 vol. % fetal bovine serum (Corning) and 1 vol. % penicillin-streptomycin (Corning). The cells were passaged using 0.25% trypsin-EDTA (Corning) and seeded at 50-80% confluence in T-175 flasks for at least 24 h before adding serum-free medium containing 1 wt % BSA. The conditioned medium was removed after 3 days and centrifuged at 300×g, then 12,000×g to remove cells and other large debris. The resulting supernatant was passed through a 0.2 µm membrane filter, concentrated to ⅓$^{rd}$ the original volume, and ultracentrifuged at 120,000×g using a Beckman Type 45Ti rotor. The collected pellet was washed with PBS and centrifuged again before resuspending in PBS for storage at −80° C. Exosome concentration was determined by BCA assay.

Western blotting was used to verify the presence of EGFR and HER2 within exosomes. Exosomes were lysed by mixing with an equal volume 2× radioimmunoprecipitation assay buffer (150 mM NaCl, 1% NP-40, 1% sodium deoxycholate, 0.1% SDS, 50 mM Tris-HCl, 2 mM EDTA, pH 7.5) containing protease inhibitors (Protease Inhibitor Cocktail II, Sigma-Aldrich). 15 µg of total protein from the lysed exosomes were separated through SDS-PAGE and transferred to a PVDF membrane. Exosome lysates were treated with antibodies for EGFR (R&D Systems), HER2 (R&D Systems), EpCAM (R&D Systems), CD63 (R&D Systems), CD81 (Santa Cruz), and CD9 (Santa Cruz). Exosomes isolated from another breast cancer cell line, MCF-7 (ATCC), were used as validation.

RNA Assay: Microplates were functionalized with a nominal concentration of 5 µgml$^{-1}$ reduced antibody: either anti-CD63 (R&D Systems MAB5048) or an equal mixture of anti-EGFR (R&D Systems AF231) and anti-HER2 (R&D Systems AF1129). Cultured exosomes were resuspended in L15 medium to a concentration of 20 µg/ml determined by microBCA assay and incubated overnight on the plate at 4° C. Total RNA was quantified using a Qubit® high sensitivity RNA assay kit (Thermo Fisher) and a microplate reader at 630 nm excitation, 680 nm emission.

Figure 11:
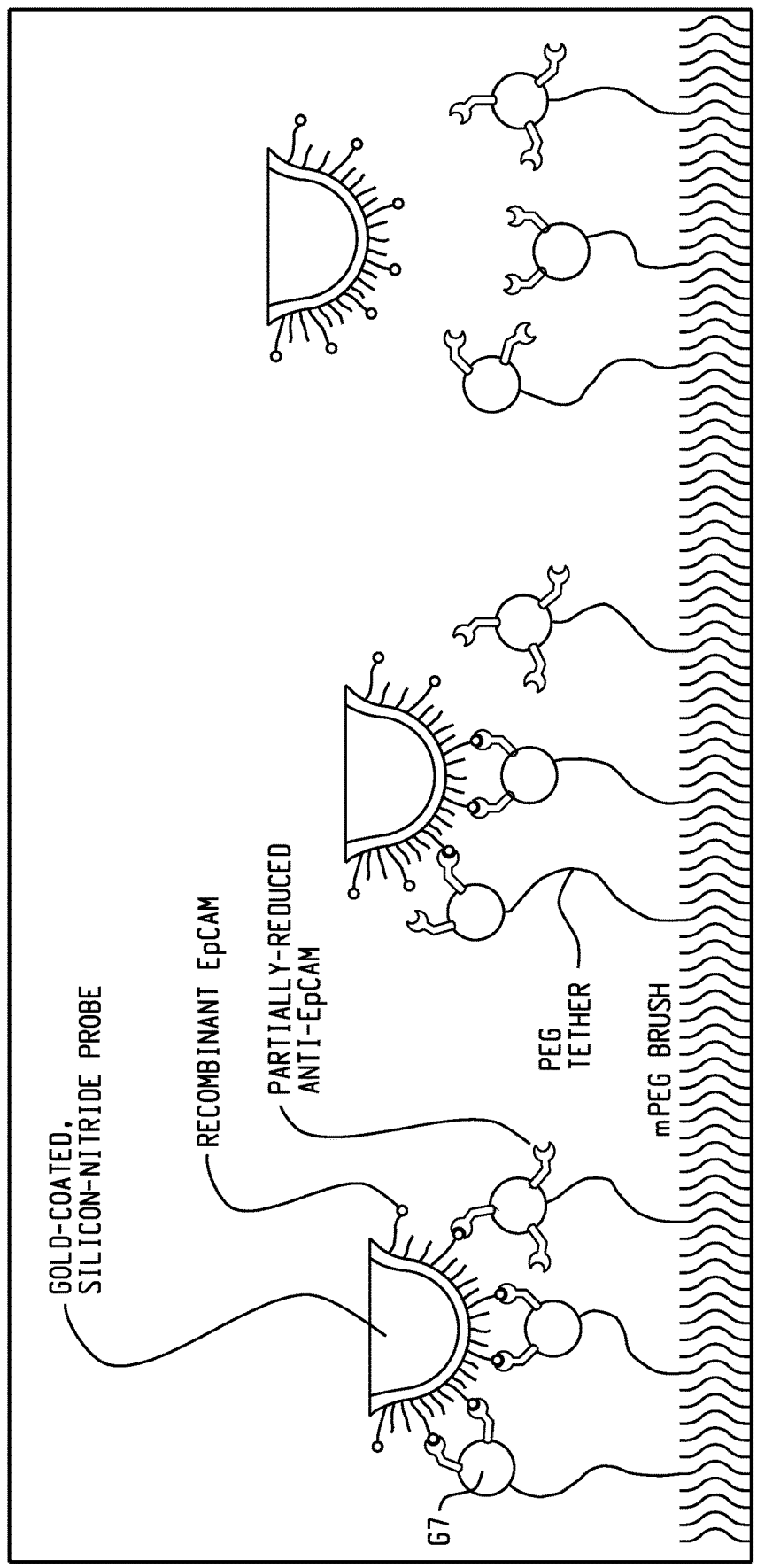
FIG. 11 is a concept illustration for detecting multivalent unbinding with AFM. A probe, nominally 180 nm in diameter and functionalized with EpCAM, was brought in contact with the capture surface and retracted at 500 nm/s. From left-to-center, two unbinding events occur and from center-to-right, three unbinding events occur as the probe retracts. Discrete ruptures of one or several EpCAM antibody pairs were detectable as abrupt changes in probe deflection.
Figure 13A:
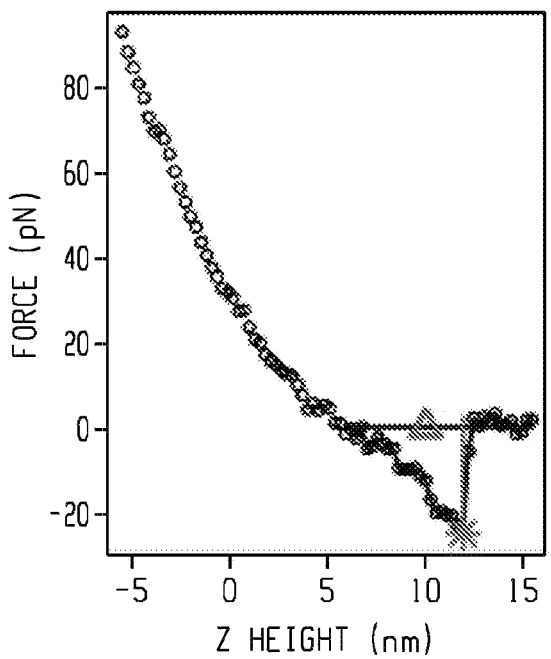
FIGS. 13a-d show representative retraction curves from nonfunctionalized G7-PEG-G7 surfaces (FIGS. 13a and b) and functionalized PEG-Ab surfaces (FIGS. 13c and d). The G7-PEG-G7 surfaces tended to exhibit significant nonspecific interaction, defined as <12 nm from the contact point (denoted by the triangle). Functionalized surfaces tended to exhibited rupture events beyond 12 nm. Detected rupture events are denoted by the star, with vertical line denoting magnitude. The continuous grey line denotes the region used for work calculation.
Figure 13B:
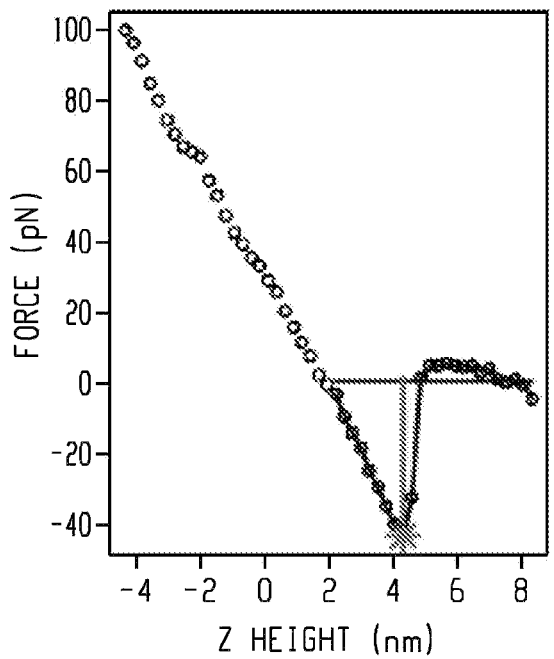
Figure 13C:
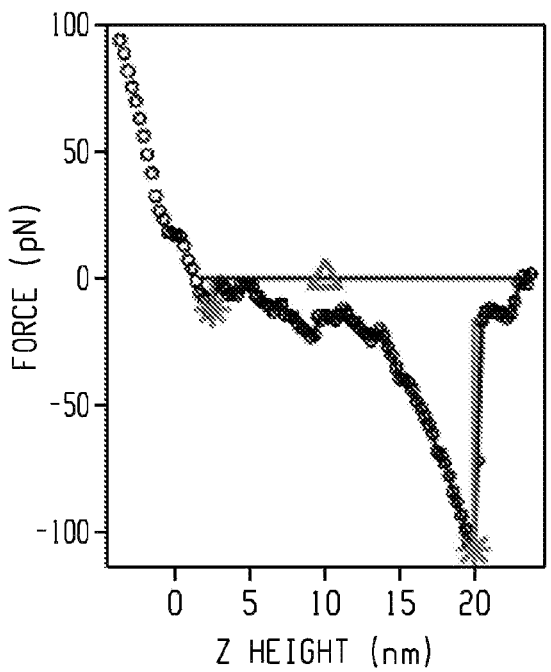
Figure 13D:
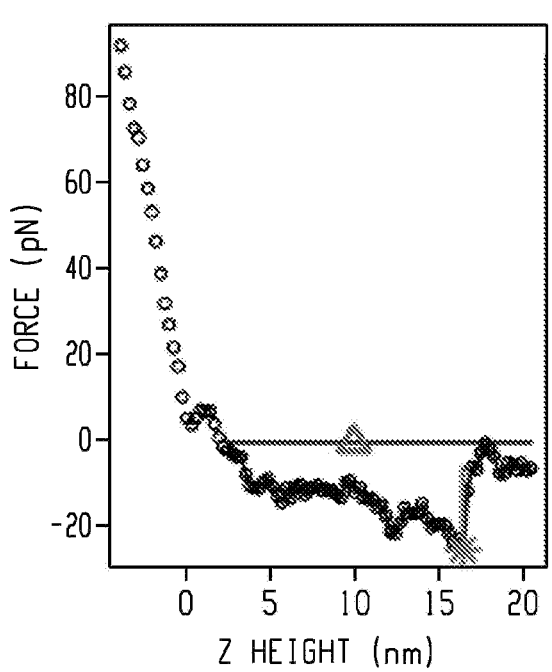

AFM Force Spectroscopy: Capture surfaces were prepared on epoxide-functionalized slides with an antibody targeting EpCAM (R&D Systems MAB960) at 5 µg/ml. A single gold-coated silicon nitride probe (Bruker NPG) was treated with a mixture of 0.1 mg/ml 7500 MW carboxyl-PEG-thiol (JenKem) and 1.9 mg/ml 5000 MW methoxy-PEG-thiol (JenKem) in DDI water for 1 h. Surfaces consisted of an -mPEG control, -PEG with partially reduced antibodies, nonfunctionalized -PAMAM-PEG-PAMAM, and -PAMAM-PEG-PAMAM-Ab functionalized with partially reduced antibodies. The probes were activated with EDC and NHS before adding recombinant human EpCAM (R&D Systems 960-EP) at 5 µg ml$^{-1}$ overnight at 4° C. Optical lever sensitivity was determined by indenting on a rigid control surface, and spring constant determined by the thermal noise method. The spring constant was determined to be 6.85 pN nm$^{-1}$. FIG. 11 shows a concept illustration for detecting multivalent unbinding with AFM.

Experiments were conducted using an Asylum Infinity™ Bio system (Oxford Instruments) with probe and sample submerged in PBS. Each surface was engaged in 5 discrete locations with 15 force curves collected at each. Force curves consisted of a 1 µm approach at 500 nm/s, 5 s dwell with the cantilever in light contact with the surface (0.2 V setpoint), and retract velocity at 500 nm/s. Data collection was at 2 kHz.

The number, distance, and magnitude of rupture events, and the work required to separate the probe from the surface, were calculated using a custom script in R utilizing "IgorR" and "Shiny" packages. The data were corrected for virtual deflection and the contact point set to (0,0) using the virtual deflection fit and a line fit to the contact region. Rupture events were defined as abrupt changes in deflection greater than 5× the RMS of deflection far from the surface. Work was defined as the area of the probe separation (z-deflection) curve below zero deflection (i.e., the adhesive region).

Statistical Analysis: All assays were compared by one- or two-way analysis of variance with Tukey post-hoc means testing using R software, assuming $p<0.05$ to be significant. Force spectroscopy results were compared using non-parametric Kruskal-Wallace tests because the data did not conform to a normal distribution. Pairwise comparisons were made using Nemenyi post-hoc tests from the R package "PMCMR." All charts were created in R with the "ggplot2" package.

Example 1: Preparation of Capture Surfaces

Capture surfaces for the capture of exosomes included epoxide-functionalized glass coated with partially-carboxylated, generation 7 (G7), poly(amidoamine) dendrimer nanoparticles. The G7 layer was functionalized with a mixture of heterobifunctional polyethylene glycol tethers (PEG) and shorter methoxy-PEG to minimize nonspecific interactions. The PEG tethers were then capped with G7 (FIG. 2). Preliminary experiments with 200 nm functionalized polystyrene beads suggested that a mixture of 0.5 µM 20,000

MW carboxy-PEG-amine, 2 µM 5,000 MW carboxy-PEG-amine, and 240 µM 2,000 MW methoxy-PEG-amine (1:1:48 by mass concentration) resulted in adequate capture rates (FIG. 3). In previous work, antibodies conjugated to PEG-tethered poly(amidoamine) (referred to here as PEG-G7) were shown to be more effective in capturing circulating tumor cells compared with controls with PEG alone (-PEG). In this work, surfaces pre-coated with polyamidoamine are referred to as G7-PEG-G7.

Figure 4A:
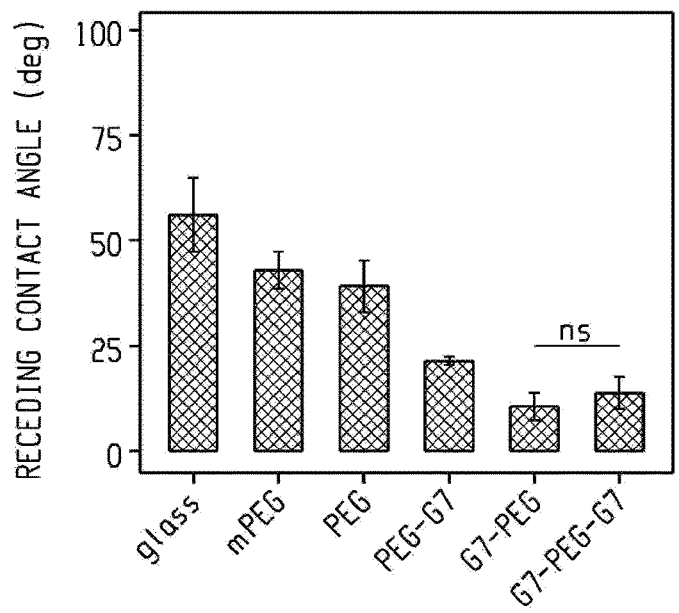
FIGS. 4a-c show dendrimer coatings alter the hydration and topographical characteristics of the capture surfaces.
Figure 4B:
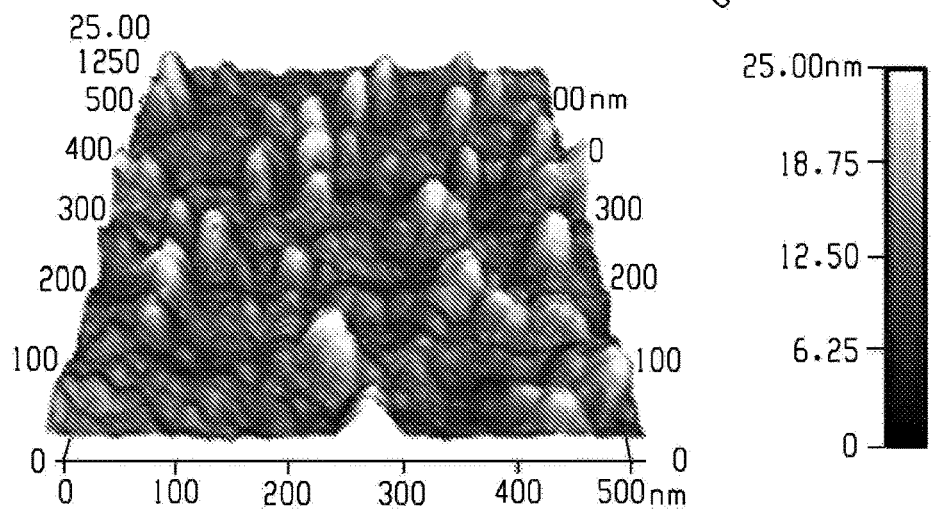
Figure 4C:
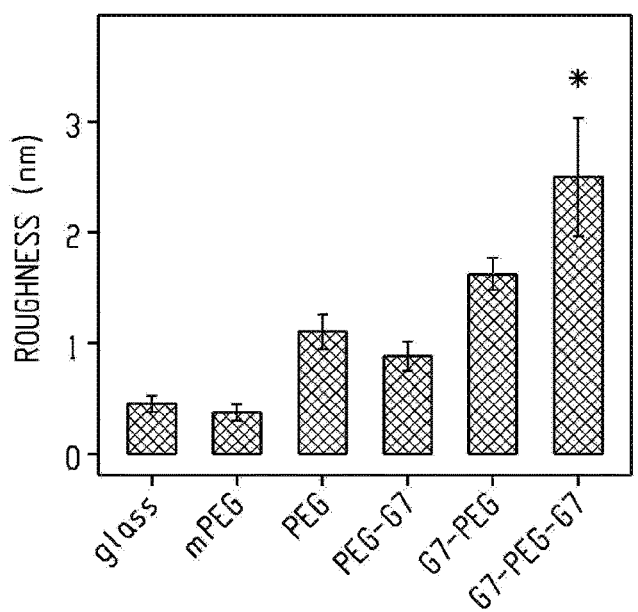
Figure 6A:
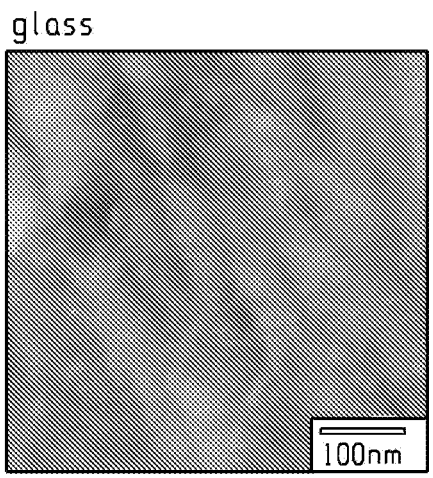
FIGS. 6a-f show representative height profiles of polymer-coated surfaces.
Figure 6B:
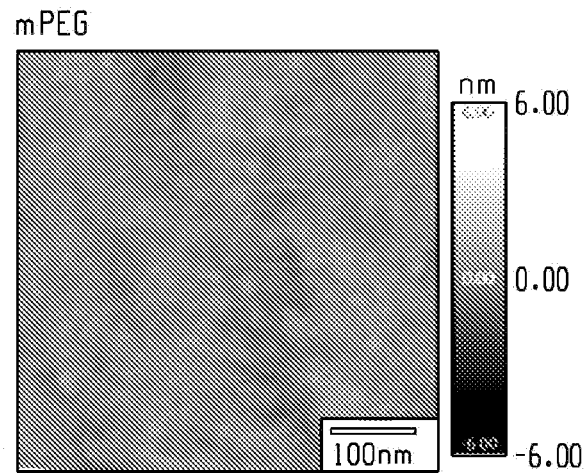
Figure 6C:
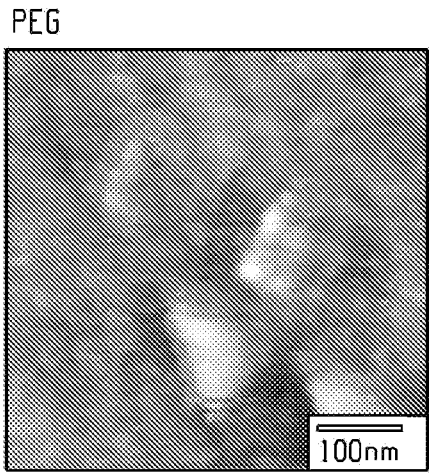
Figure 6D:
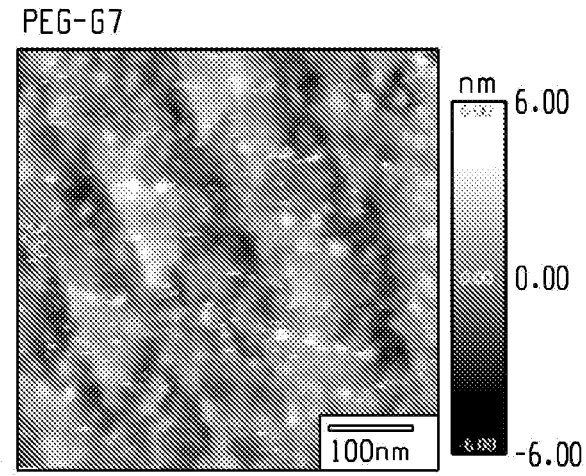
Figure 6E:
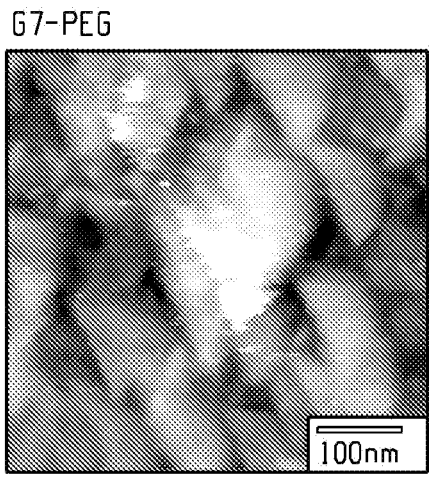
Figure 6F:
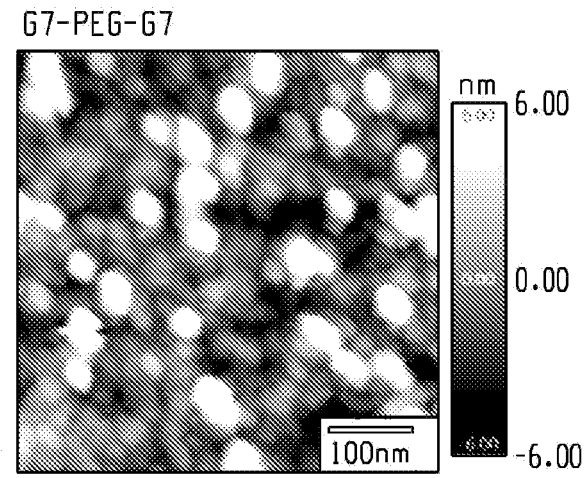

Successful surface functionalization was demonstrated by contact angle measurements and atomic force microscopy (AFM) imaging. These measurements revealed distinct differences in the physical properties of G7-PEG-G7 surfaces compared to PEG-G7 surfaces. Receding contact angles of ultrapure water collected using the sessile drop technique showed that: i) all polymer surfaces were more hydrophilic than the basal glass substrate ($p<0.01$); ii) surfaces containing G7 PAMAM dendrimers were more hydrophilic than those with PEG alone ($p<0.01$); and iii) surfaces with the bottom layer of dendrimers were even more hydrophilic than those without dendrimers as the first layer ($p<0.01$, FIG. 4a, FIG. 5). FIG. 4b shows the topography of a G7-PEG-G7 surface with nanoscale features. Surface roughness (Rq) was calculated from AFM images (500 nm×500 nm scans) of hydrated samples using a silicon nitride cantilever with nominal radius of 2 nm. The roughness of the surfaces pre-coated with dendrimers was significantly greater than mPEG and PEG surfaces (~2.5 vs. ~1 nm, $p<0.05$, FIG. 4c, FIG. 6). Note that the contour lengths of the PEG tethers were significantly longer than the reported roughness over 150 nm for the 20 kDa tether and so should the ability to extend capture antibodies much higher above the surface than the surface profile measurements indicate. The AFM was unable to resolve such flexible features. Instead, the measured roughness values likely reflect the topography of the underlying glass or G7-coated glass substrates and were consistent with previously-reported dimensions for surface-adsorbed PAMAM dendrimers. Nonetheless, the two sets of surface measurements indicate the surfaces were successfully modified with sequential addition of the polymer layers.

Example 2: Exosome Capture

Figure 7A:
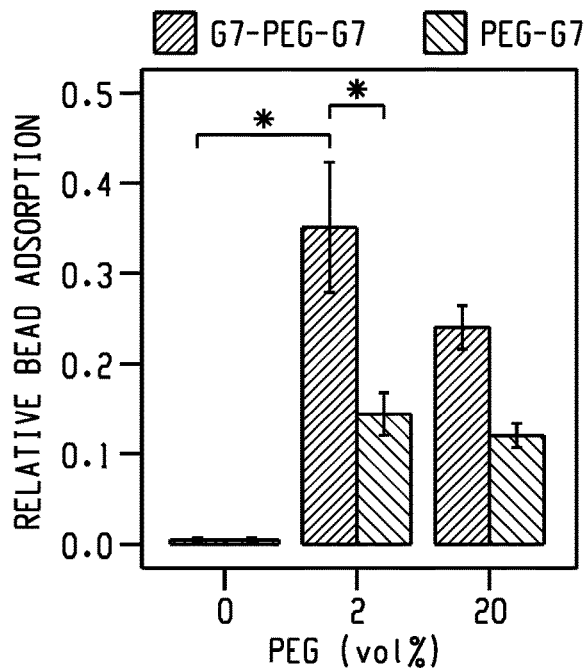
FIG. 7a shows relative capture of 200 nm fluorescent beads is the greatest on 2% PEG surfaces with G7-PEG-G7 configuration.

The various polymer surface configurations were initially screened using exosome-sized beads. Polystyrene beads nominally 200 nm in diameter (Thermo Fisher Fluo-Sphere™) were coated with recombinant Epithelial-Cell-Adhesion-Molecule (EpCAM, R&D Systems), a commonly-targeted surface antigen for circulating tumor materials. Capture surfaces with various G7 dendrimers and PEG configurations were functionalized with antibodies against EpCAM (aEpCAM, R&D Systems). Our results shown in FIG. 7a revealed significantly higher capture efficiency, as measured by increased fluorescent intensity, on the surfaces with two layers of dendrimers (G7-PEG-G7), compared to those with a single layer of dendrimers (PEG-G7). This enhancement was mostly pronounced when 2% of tethering, longer PEG (20 kDa) was added on the surface with shorter PEG (5 kDa), which shows an agreement with our previous observation using micelles. An increase of the content of the tethering PEG (5-20%) did not result in a further enhancement of capture efficiency.

Figure 7B:
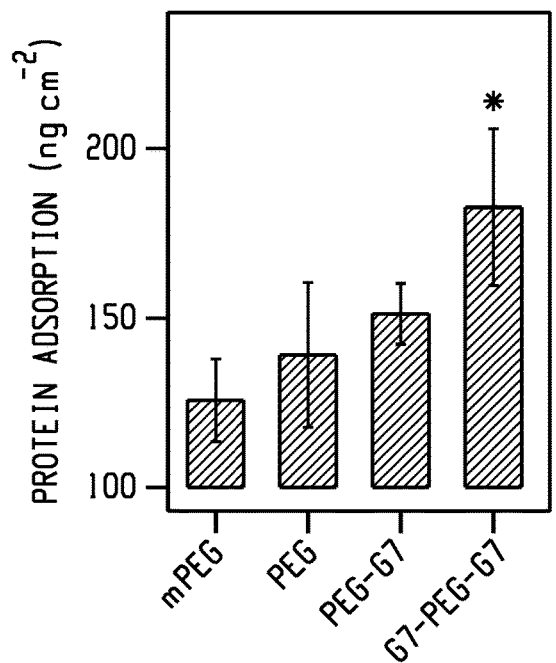
FIG. 7b shows relative capture of exosomes from healthy human serum quantified by total protein adsorption on surfaces functionalized with aCD63.

To test the capture of nanoscale vesicles from healthy human serum, we functionalized the surfaces against CD-63, a commonly-targeted surface marker unique to exosomes and incubated the capture surfaces with filtered human serum (Sigma Aldrich). As shown in FIG. 7b, a bincinchoninic acid assay (Thermo Fisher BCA assay kit) showed 1.71 cm$^{-2}$ (standard deviation 0.55) of protein adsorbed onto the aCD63-functionalized G7-PEG-G7 surfaces, an amount 2.5 times greater than mPEG surfaces and higher than aCD63-functionalized PEG ($p<0.01$) and 1.7 times greater PEG-G7 capture surfaces ($p=0.02$). Adsorbed protein was 4.5 fold higher than mPEG controls ($p<0.01$) and 9.7 fold higher than non-functionalized G7-PEG-G7 ($p<0.01$). The antibody coating itself, in the absence of serum, was beneath the sensitivity limit of the assay and statistically similar to mPEG controls ($p=0.89$). These results indicate that a surface coating with two layers of dendrimer exhibits the highest capture efficiency for both beads and exosomes from human serum.

Figure 7C:
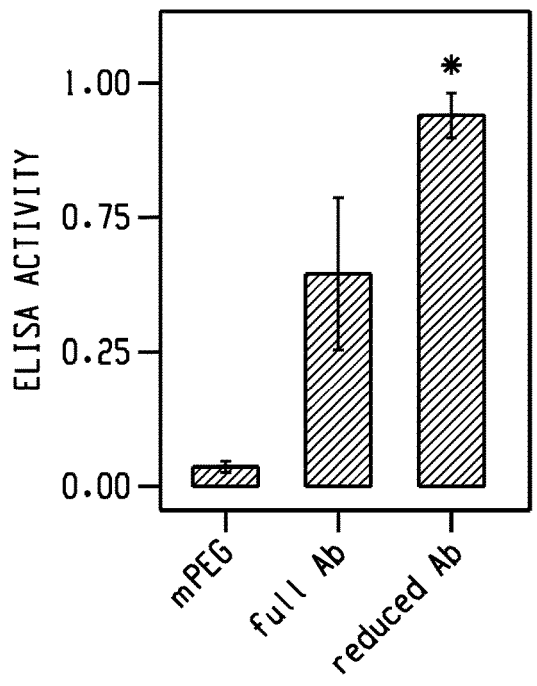
FIG. 7c shows confirmation of exosome capture from healthy human serum on the aCD63-immobilized surfaces quantified using ELISA targeting CD81. This results demonstrate the benefit of using reduced capture antibodies.
Figure 7D:
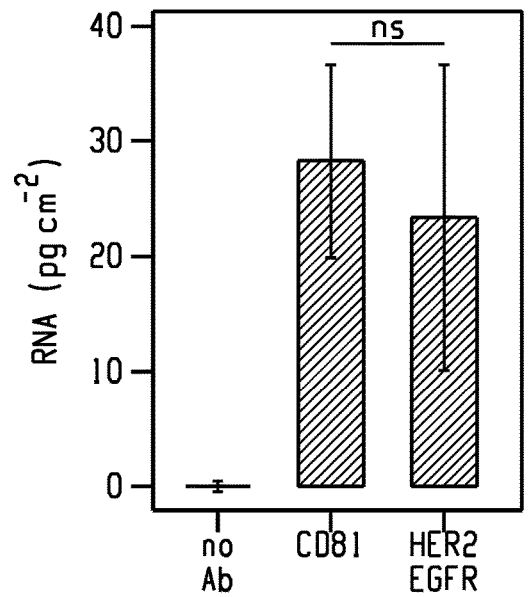
FIG. 7d shows a comparison of capture of cultured exosomes between surfaces functionalized against a tetraspanin (CD81) and against cell surface markers (HER2 and EGFR). Both surfaces display significantly higher capture than the surface without any antibodies, despite the statistically insignificant difference between the functionalized surfaces. Bars show mean +/−standard deviation, * indicate p<0.05 pairwise comparisons with all other groups, while 'ns' indicates no statistical difference between groups.
Figure 8A:
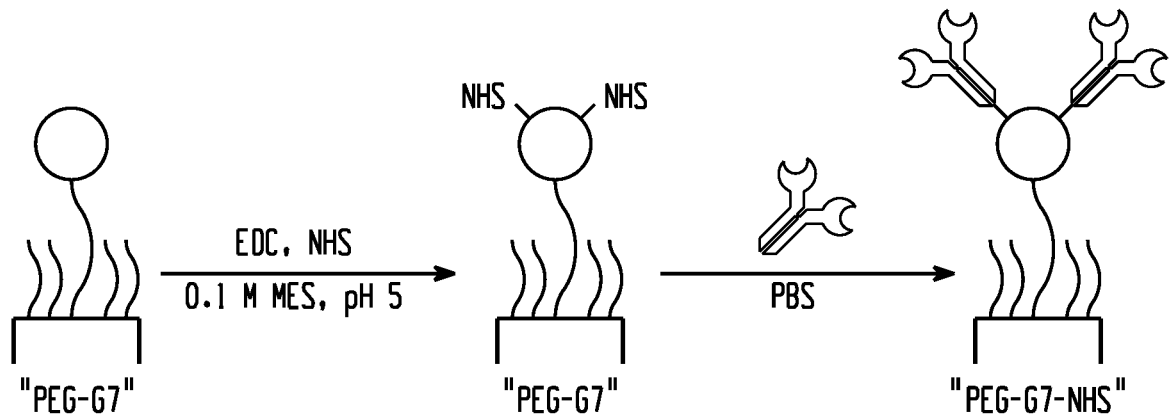
FIGS. 8a and b show an antibody conjugation strategy.
Figure 8B:
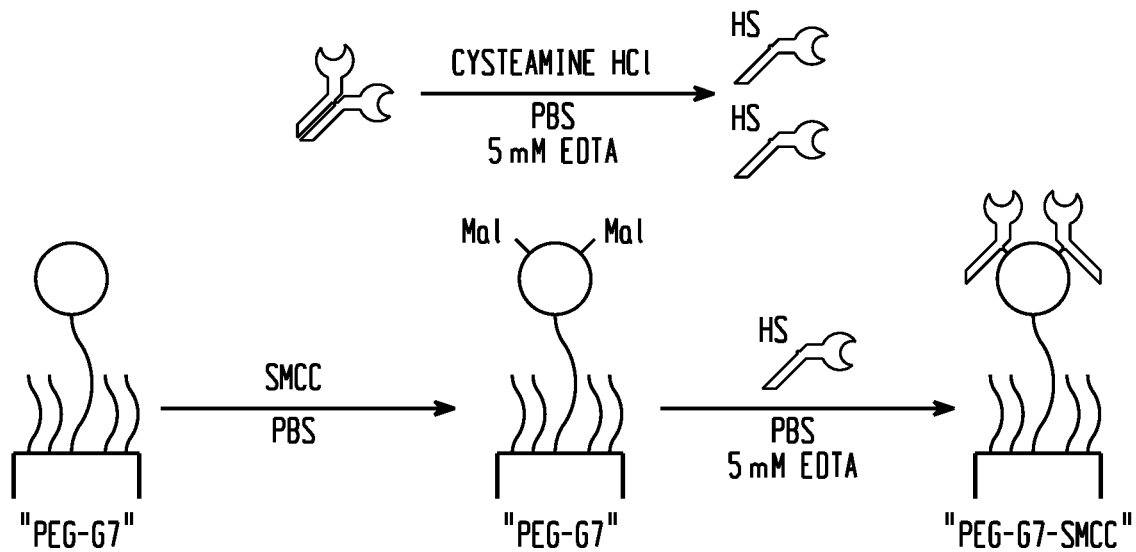
FIG. 8b shows conjugation of partially-reduced antibodies to amine groups of a PEG-G7 surface.

We further hypothesized that exosome capture could be increased by coating the G7-PEG-G7 surface with partially-reduced antibodies (FIG. 8). In this configuration, antibodies reduced by cysteamine hydrochloride conjugate to surfaces activated with sulfosuccinimidyl 4-(N-maleimidomethyl)cyclohexane-1-carboxylate (SMCC) through sulfhydryl groups in the hinge region. Full antibodies were covalently linked using methods consistent with our previous work. Briefly, the PEG- or G7 PAMAM dendrimer-coated surfaces were activated with 1-ethyl-3-(3-dimethylaminopropyl)carbodiimide (EDC) and N-hydroxysuccinimide (NETS) before reaction with the capture antibody of interest through conjugation with lysine residues, resulting in random conjugation. Compared to full antibodies, the reduced antibodies may have a more consistent orientation, and their smaller size may facilitate greater conformational flexibility to form multivalent attachments. Herein, surfaces functionalized with full and reduced aCD63 were assessed using human serum. In this test, we used an enzyme-linked absorbance assay (ELISA) to quantitatively compare surface configurations. The ELISA assay is more sensitive than the BCA assay above. Moreover, since we targeted a second exosome-specific tetraspanin (CD81), the test provided further confirmation of functional exosome capture. Results showed a significant benefit to reduced antibodies (FIG. 7c), with a 1.7 fold increase in signal ($p<0.01$) over G7-PEG-G7 surfaces with full antibodies. Finally, to confirm that the reduced antibodies can be surface immobilized at a sufficient density to mediate multivalent binding effect, a fluorescent-labeled antibody was employed to measure the surface coverage. Human immunoglobulin G (IgG) used as a model antibody was labeled with an amine-reactive fluorophore (Thermo Fisher AlexaFluor405-NHS), partially reduced, and conjugated to the G7-PEG-G7 capture surface via SMCC. The fluorescent signal revealed a coating density of 177±78 ng cm$^{-2}$. This density corresponds to ~140 binding sites within a 100 nm×100 nm square.

Figure 9:
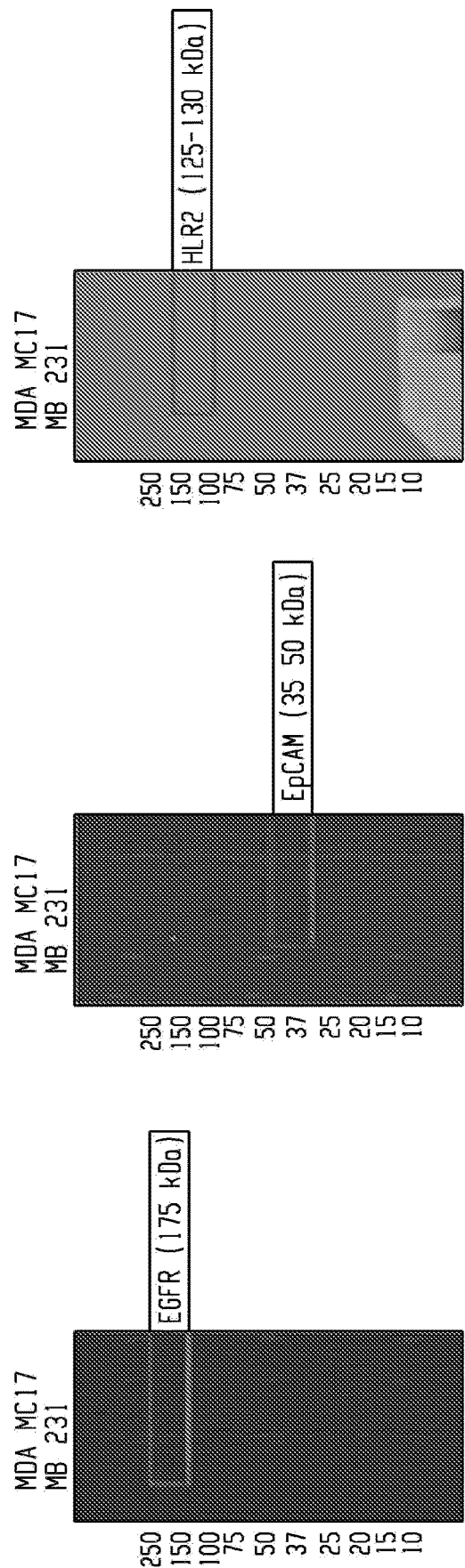
FIG. 9 shows Western blotting confirmed the presence of cancer cell surface markers EGFR and HER2, but not EpCAM on MDA-MB-231-derived exosomes.
Figure 10:
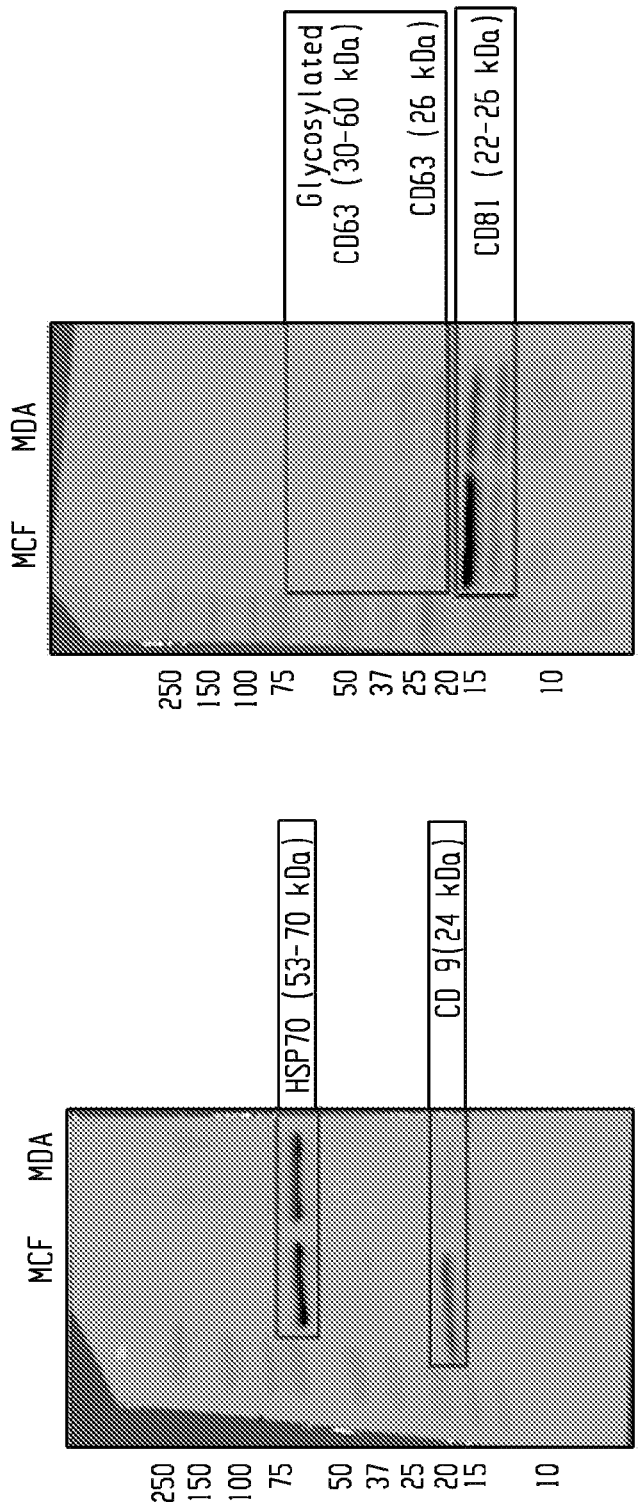
FIG. 10 shows Western blotting confirmed the presence of tetraspannins CD81 and CD9 that differentiate exosomes from similarly-sized extracellular vesicles in MDA-MB-231-derived exosomes.

Next, we sought to demonstrate the ability of G7-PEG-G7 surfaces to isolate exosomes using various surface markers, and to show that RNA could be isolated from the surface. We evaluated whether surfaces could efficiently capture exosomes produced by cancerous cells by both an exosome-specific transmembrane protein (CD81) and by a mixture of surface markers overexpressed by metastatic breast cancer cells: epidermal growth factor receptor (EGFR) and human epidermal growth factor receptor 2 (HER2). Western blotting confirmed the presence of EGFR and HER2 (FIG. 9) and the exosome markers CD81 (FIG. 10) in exosomes collected from cultured MDA-MB-231 cells. Unlike many tumor-derived cells such as MCF-7, MDA-MB-231 cells do not express EpCAM at high levels (FIG. 9). CD63 was not targeted, as western blotting showed this tetraspanin was expressed at lower rates than CD81 in these culture-derived vesicles. Exosomes were isolated from conditioned media by ultracentrifugation[23], resuspended to 20 μg/ml protein based on BCA assay, and incubated over the capture surfaces at 4° C. overnight. The surfaces functionalized with reduced aCD81 and the mixture of cancer surface markers captured 25.9 and 21.6 pg cm⁻RNA, respectively (FIG. 3d), with no statistical difference between the two surfaces (p=0.92).

Finally, to demonstrate the capture of RNA in quantities sufficient for downstream analysis by increasing the capture surface area, fiberglass filters (Millipore 25 mm diameter, nominal 1.2 μm pore size) were functionalized with the optimized capture surface and a mixture of reduced aCD63 and aCD81. The larger surface area within the filters allowed for a higher capacity of exosome capture compared with the flat glass surfaces described above. The filters were incubated with 1 mL human plasma diluted with 1 mL PBS under agitation for 1 h. A mean of 9.77 ng RNA (standard deviation 2.04) were captured in each filter, a capture efficiency on par with highly efficient microfluidic techniques, and an order of magnitude more efficient than ultracentrifugation.

For mechanistic understanding of the observed surface capture behaviors, we then employed AFM force spectroscopy to characterize the molecular mechanisms responsible for high capture rates by G7-PEG-G7 surfaces. This technique is sensitive enough to detect the forces of antibody-antigen unbinding and has been used to resolve multivalent unbinding between ligand-functionalized dendrimers and immobilized proteins. A gold-coated, silicon nitride probe was functionalized with recombinant EpCAM attached via carboxy-PEG-sulfhydryl tethers. The probe had a nominal diameter of 60 nm and an experimentally-determined spring constant of 6.52 pN nm⁻¹ (Bruker Probes NPG-D). Force spectroscopy was conducted on an Asylum MFP-3D Infinity™ Bio system (Oxford Instruments). The functionalized probe was brought in contact with each surface for 5 s with approach and retraction speeds of 500 nm s⁻¹. A total of 75 force curves were collected from each surface in five separate locations, and analysis was completed with custom-scripted code. Representative force curves are shown in FIG. 12a-c.

The energy required to pull the functionalized AFM probe off the capture surface was significantly higher on G7-PEG-G7 with aEpCAM (noted as G7-PEG-G7-Ab) compared with all other surfaces (p<0.01, FIG. 12d), with a median of 1,980 pN nm (mean 2,500, standard deviation 2,540). The PEG surfaces with aEpCAM (PEG-Ab) required significantly greater energy than PEG without aEpCAM (p<0.01) and slightly lower than nonfunctionalized G7-PEG-G7 (p=0.06). The functionalized PEG surfaces required a median of 710 pN nm (mean 1,510, standard deviation 2,140) to separate the probe, compared to a median of 240 pN nm and 390 pN nm for nonfunctionalized PEG and G7-PEG-G7 controls, respectively.

Figure 14A:
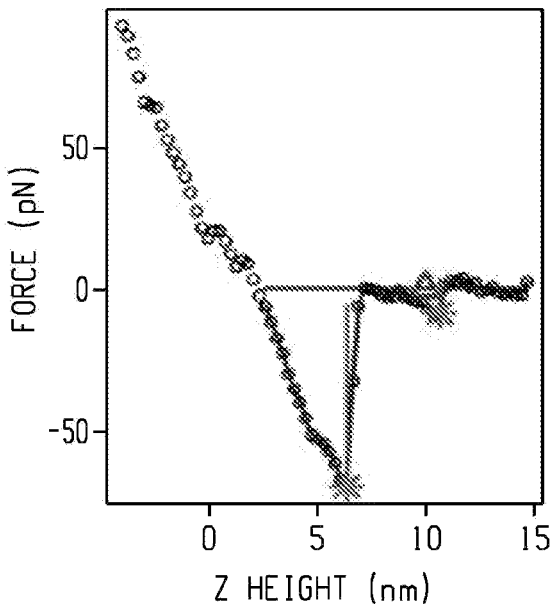
FIGS. 14a-d show representative retraction curves from functionalized G7-PEG-G7-Ab surfaces demonstrating multivalent unbinding. Selected curves show 2 (14a), 3 (14b), 4 (14c), and 6 (14d) discrete unbinding events.
Figure 14B:
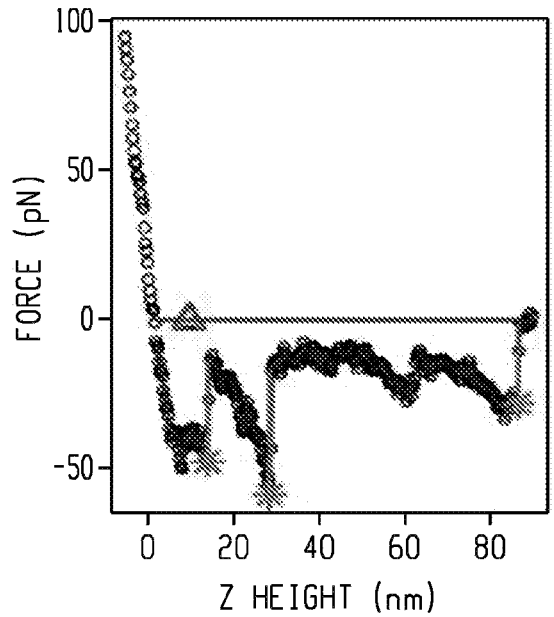
Figure 14C:
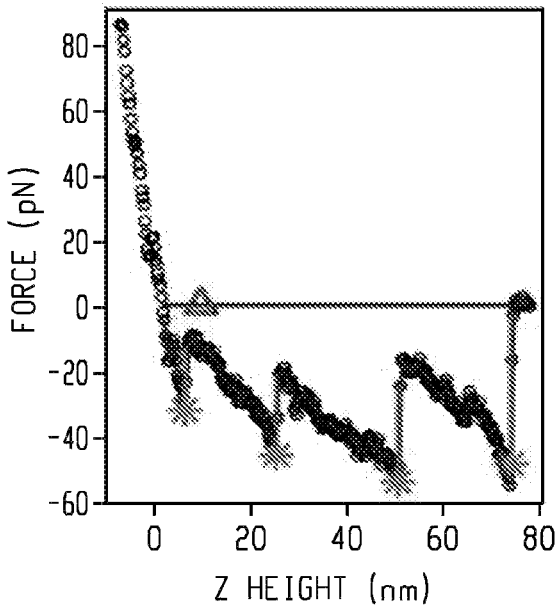
Figure 14D:
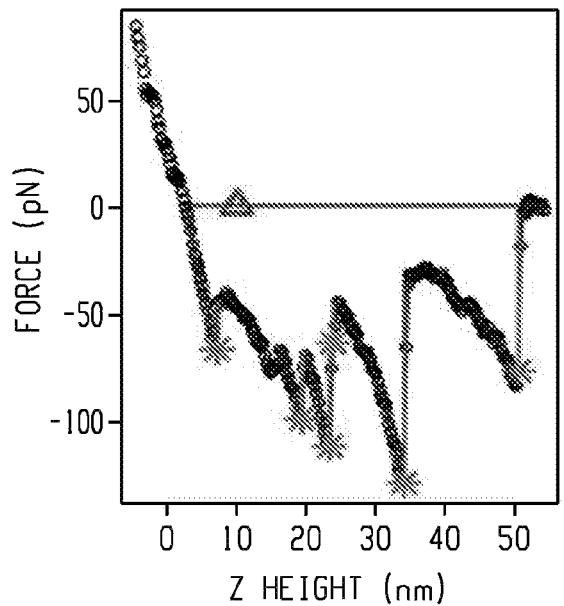
Figure 15A:
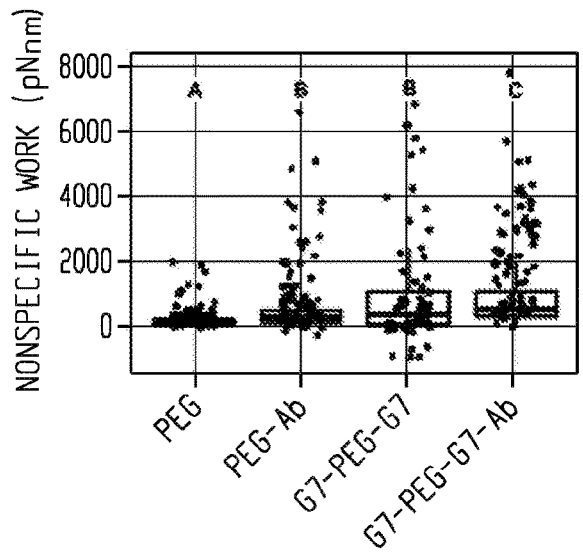
FIGS. 15a-d show AFM force spectroscopy measurements.
Figure 15B:
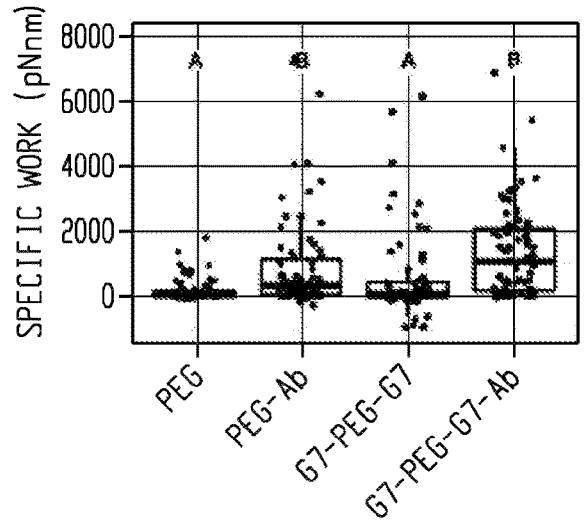

We observed significantly greater energy of binding on nonfunctionalized G7-PEG-G7 surfaces compared to nonfunctionalized PEG (p=0.05, FIG. 12d), despite neither surface containing antibodies that would bind with high specificity to EpCAM on the probe. Most of this adhesive energy was in close proximity to the contact point, indicative of interactions between polymer coatings through formation of secondary intermolecular forces (FIG. 13, 14a,b). In contrast, both surfaces with aEpCAM exhibited the characteristic strain behavior of a highly flexible linker prior to rupture (FIG. 13, 14c,d). Based on these observations, we conservatively defined nonspecific work as that done within 12 nm of the contact point, equal to twice the Flory radius of the shorter, 5 kDa tethers. The work required to lift the probe up to 12 nm on G7-PEG-G7 surfaces was similar to that of PEG-Ab (p=0.96) and approaching that of G7-PEG-G7-Ab (p=0.03, FIG. 15a). Above 12 nm, in contrast, PEG-Ab surfaces showed significantly higher adhesive energy than G7-PEG-G7 (p<0.01, FIG. 14b). Similar "nonspecific" interactions between dendrimers and proteins have been previously reported in AFM experiments and attributed to van der Waals forces and electrostatic interactions. We conclude that the nonspecific adhesion observed here was due to the high surface density of polymer chains and dendrimers on G7-PEG-G7 surfaces.

Figure 15C:
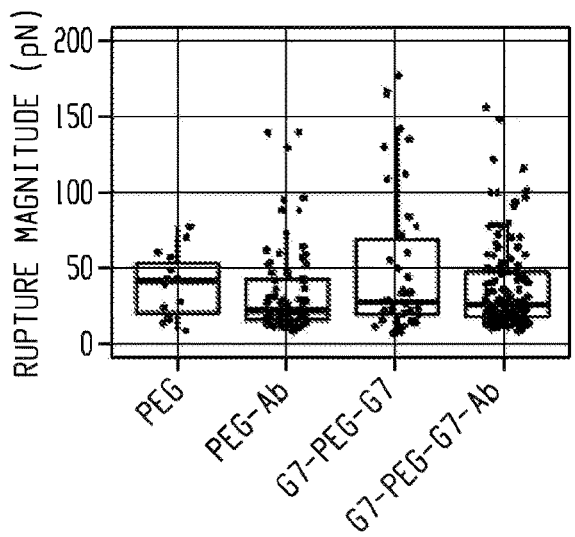
Figure 15D:
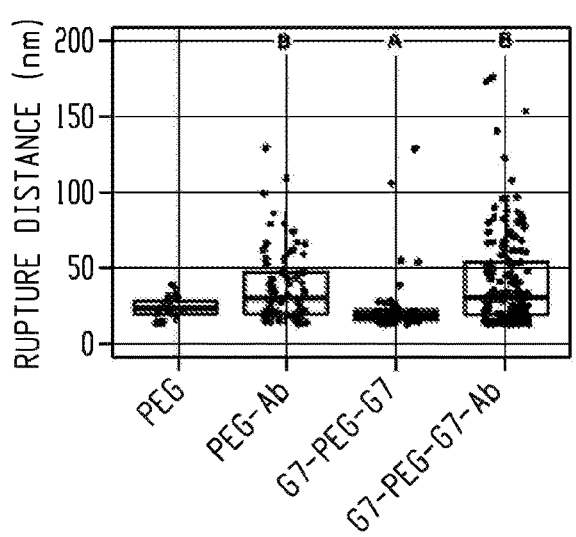
Figure 16:
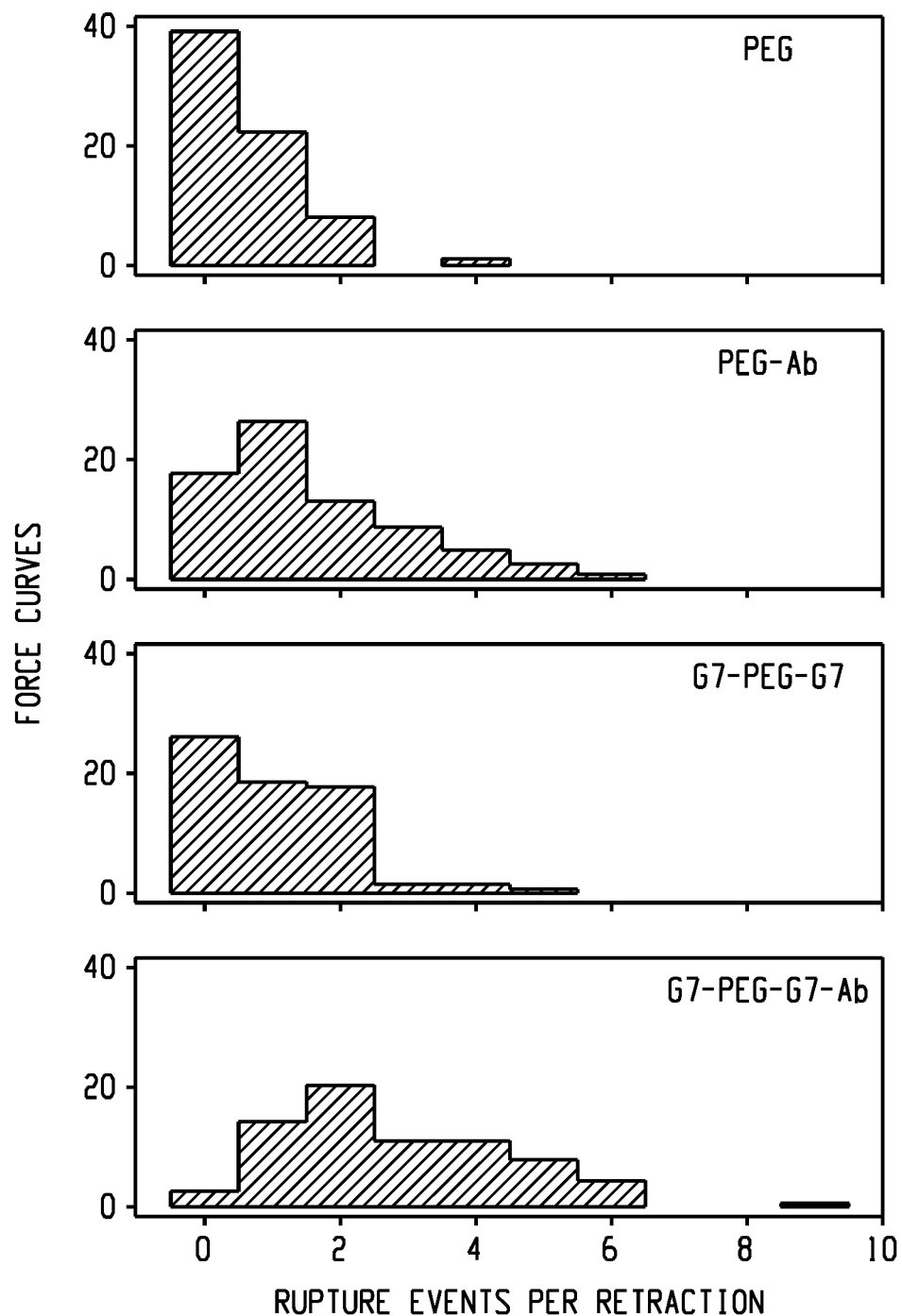
FIG. 16 shows quantification of multivalent binding measure using AFM force spectroscopy. The number of discrete rupture events per retraction averaged 2.9 on functionalized G7-PEG-G7 compared to 1.6 on functionalized PEG controls. The rupture events are defined as abrupt changes in deflection corresponding to an approximately 8 pN magnitude.

The sensitivity and selectivity of immunoaffinity capture methods are enhanced when multiple antibodies are able to interact with the analyte because multivalent binding dramatically lowers the dissociation rate. Hyperbranched dendrimers facilitate multivalent capture in two ways: a high density of functional groups allows for multiple antibodies to be conjugated to each 9 nm diameter nanoparticle, and the branched structure allows for conformational flexibility for the ideal orientation of binding domains. To quantify the multivalent binding effect at the nano-scale, we counted the number of abrupt ruptures, characteristic of antibody-antigen unbinding events in force spectroscopy. These events were defined as abrupt changes in deflection more than five times the root mean square of the deflection signal away from the surface, approximately 8 pN in magnitude. The number of such rupture events per retraction was significantly greater on the antibody-functionalized G7-PEG-G7-Ab surfaces compared to all others (p<0.01, FIG. 16). These capture surfaces exhibited a median of 2.9±1.8 rupture events per curve compared to 1.6±1.5 for PEG-Ab. Rupture event magnitude ranged from 8 to 370 pN (mean 39 pN), with no statistical difference in magnitude across capture surfaces (FIG. 15c). Others have reported antibody-antigen rupture forces of 60 pN. Rupture distance was also significantly greater on G7-PEG-G7-Ab than on controls (p<0.01), indicative of specific antibodies unbinding after polymer extension (FIG. 15d). The AFM results suggest that the performance of G7-PEG-G7-Ab capture surfaces were attributable to the ability to form multivalent antibody interactions, reinforced with nonspecific adhesion from the dendrimer coating.

Multivalent immunocapture of exosomes is difficult due to the exceptionally small size of the vesicles. Here, we report three significant findings in re-engineering a surface designed for multivalent immunocapture from the micron scale to the nanoscale. First, the initial coating of G7 PAMAM dendrimers resulted in a more hydrated surface with nanometer scale features and a potentially greater number of functional sites for PEG attachment compared to the underlying glass. Second, the addition of longer, 20 kDa tethers improved binding site flexibility compared to 5 kDa tethers alone. Finally, partially-reduced antibodies conjugated to G7 dendrimers via SMCC outperformed full antibodies conjugated via NHS. These three factors all contributed to the highly sensitive and specific exosomes capture we report herein.

Without being held to theory, the exosome capture surface described herein exhibited three notable differences from our previously-described cell capture surfaces that improve multivalent binding at the nanoscale. A pre-coating of polyamidoamine dendrimer resulted in a more hydrated surface with nanometer scale features and a potentially greater number of functional sites compared to the underlying glass. Second, the addition of longer, 20,000 MW tethers improved binding site flexibility compared to 5,000 MW tethers alone. Finally, partially-reduced antibodies conjugated to PAMAM via SMCC outperformed full antibodies conjugated via NHS. The smaller half-antibodies likely exhibited greater conformational flexibility compared to the full versions, and the orthogonal chemistry avoided the possibility of crosslinking neighboring nanoparticles to each other.

The development of liquid biopsies based on exosomal material requires new technologies capable of separating tumor-derived exosomes with high specificity and efficiency. The polyamidoamine dendrimer-coated surfaces described herein enhanced the immunoaffinity capture of nanoscale exosomes through multivalent binding. Protein, ELISA, and RNA assays demonstrated enhanced capture compared to linear PEG controls. Enhanced multivalent binding was demonstrated using AFM force spectroscopy. The results corroborate previous results showing that multivalent binding by dendrimers enhanced capture of cancer cells and confirm that the effect can be extended to the nanoscale.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A cancer biomarker capture surface comprising
a substrate having a surface,
a first plurality of nanoparticles directly attached to the substrate surface,
a plurality of methoxy poly(ethylene glycol) polymer brush molecules attached to a first portion of the first plurality of nanoparticles on the substrate surface via an N-hydroxysuccinimide (NHS) functionality, wherein the plurality of polymer brush molecules comprise a single amine functionality for attachment to the first plurality of nanoparticles, do not comprise capture agent, and reduce nonspecific binding to the surface,
a plurality of poly(ethylene glycol) bifunctional tethers, wherein an amine functionality on a first end of the bifunctional tethers is attached to a second portion of the first plurality of nanoparticles on the substate surface via an NHS functionality, wherein the bifunctional tethers have a higher molecular weight than the polymer brush molecules,
a second plurality of amine functionalized nanoparticles attached via an NHS functionality of at least a portion of the plurality of the second ends of the bifunctional tethers, wherein the bifunctional tether connects the first plurality of nanoparticles on the substrate surface to the second plurality of nanoparticles, and
a capture agent for the cancer biomarker attached to at least a portion of the second plurality of nanoparticles via an NHS functionality,
wherein the first plurality of nanoparticles and the second plurality of nanoparticles comprise the same or a different poly(amidoamine) dendrimer (PAMAM dendrimer).

2. The cancer biomarker capture surface of claim 1, wherein the cancer biomarker is a vesicle, a cell, a protein, or a nucleic acid.

3. The cancer biomarker capture surface of claim 2, wherein the cancer biomarker is a vesicle.

4. The cancer biomarker capture surface of claim 1, wherein the plurality of bifunctional tethers comprises a mixture of low molecular weight tethers and high molecular weight tethers, wherein the low molecular weight tethers have a molecular weight of 300 to 5000 Da, and the high molecular weight tethers have a molecular weight of 5000 to 100,000 Da.

5. The cancer biomarker capture surface of claim 1, wherein the poly(amidoamine) dendrimer comprises a generation 3 PAMAM dendrimer, a generation 4 PAMAM dendrimer, a generation 5 PAMAM dendrimer, a generation 6 PAMAM dendrimer, a generation 7 PAMAM dendrimer, a generation 8 PAMAM dendrimer, a generation 9 PAMAM dendrimer, or a combination thereof.

6. The cancer biomarker capture surface of claim 1, wherein the capture agent comprises an antibody, a partially reduced antibody, an antibody fragment, a recombinant protein, a peptide, an aptamer, a small molecule, or a combination thereof.

7. The cancer biomarker capture surface of claim 1, wherein the cancer biomarker is a cancer vesicle and the capture agent specifically binds an exosome surface marker.

8. The cancer biomarker capture surface of claim 7, wherein the exosome surface marker comprises cluster of differentiation 63 (CD63), cluster of differentiation 81 (CD81), cluster of differentiation 9 (CD9), or a combination thereof.

9. The cancer biomarker capture surface of claim 7, wherein the exosome surface marker comprise a surface marker for an epithelial cancer-derived exosome, and is epithelial cellular adhesion molecule (EpCAM), epidermal growth factor receptor (EGFR), human epidural growth factor receptor 2 (HER2), cadherin 11, programmed death ligand 1 (PDL1), or a combination thereof.

10. The cancer biomarker capture surface of claim 7, wherein the exosome surface marker comprises the prostate cancer marker prostate-specific antigen (PSA) or the melanoma marker cluster of differentiation 146 (CD146).

11. A device comprising the cancer biomarker capture surface of claim 1.

* * * * *